(12) United States Patent
Greenberg et al.

(10) Patent No.: US 10,143,576 B2
(45) Date of Patent: *Dec. 4, 2018

(54) TWIN BIFURCATED STENT GRAFT

(71) Applicants: Cook Medical Technologies LLC, Bloomington, IN (US); The Cleveland Clinic Foundation, Cleveland, OH (US)

(72) Inventors: Roy K. Greenberg, Bratenahl, OH (US); David E. Hartley, Wannanup (AU); Michael Lawrence-Brown, City Beach (AU)

(73) Assignees: Cook Medical Technologies LLC, Bloomington, IN (US); The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/651,837

(22) Filed: Jul. 17, 2017

(65) Prior Publication Data

US 2017/0325978 A1    Nov. 16, 2017

Related U.S. Application Data

(63) Continuation of application No. 11/788,285, filed on Apr. 19, 2007, now Pat. No. 9,707,113.

(Continued)

(51) Int. Cl.
*A61F 2/954* (2013.01)
*A61F 2/07* (2013.01)
(Continued)

(52) U.S. Cl.
CPC ........ *A61F 2/954* (2013.01); *A61B 17/00234* (2013.01); *A61F 2/07* (2013.01);
(Continued)

(58) Field of Classification Search
CPC ...... A61F 2/954; A61F 2002/061; A61F 2/07; A61F 2/24; A61F 2/89; A61F 2220/0016;
(Continued)

(56) References Cited

U.S. PATENT DOCUMENTS

| 4,501,263 A | 2/1985 | Harbuck |
| 4,592,754 A | 6/1986 | Gupte et al. |

(Continued)

FOREIGN PATENT DOCUMENTS

| EP | 0 461 791 B1 | 6/1991 |
| EP | 0 646 365 B1 | 9/1994 |

(Continued)

OTHER PUBLICATIONS

Greenberg et al., "Beyond the Aortic Bifurcation: Branched Endovascular Grafts for Thoracoabdominal and Aortoiliac Aneurysms," 43 Journal of Vascular Surgery, No. 5, pp. 879-886 (May 2006).

(Continued)

*Primary Examiner* — Son Dang
(74) *Attorney, Agent, or Firm* — Brinks Gilson & Lione

(57) ABSTRACT

A stent graft has a tubular body with a first bifurcation with first and second legs extending from the bifurcation. One of the legs has a further bifurcation to define a side arm. The stent graft can be deployed into the vasculature of a patient with the tubular body being in an aorta of the patient, a first leg extending down an iliac artery, a second leg being directed towards a contralateral iliac artery and the side arm directed to an internal artery of one of the iliac arteries. One of the legs can include a valved aperture to enable the placement of an indwelling catheter therethrough.

16 Claims, 30 Drawing Sheets

Related U.S. Application Data

(60) Provisional application No. 60/793,282, filed on Apr. 19, 2006.

(51) Int. Cl.
*A61F 2/24* (2006.01)
*A61B 17/00* (2006.01)
*A61F 2/06* (2013.01)
*A61F 2/89* (2013.01)

(52) U.S. Cl.
CPC ...... *A61F 2/24* (2013.01); *A61B 2017/00243* (2013.01); *A61F 2/89* (2013.01); *A61F 2002/061* (2013.01); *A61F 2002/065* (2013.01); *A61F 2002/067* (2013.01); *A61F 2002/075* (2013.01); *A61F 2220/0016* (2013.01); *A61F 2220/0075* (2013.01)

(58) Field of Classification Search
CPC ........ A61F 2220/0075; A61F 2002/065; A61F 2002/67; A61F 2002/075; A61B 2017/00243; A61B 17/00234
USPC .................... 623/1.13, 1.24, 1.25, 1.28, 1.29
See application file for complete search history.

(56) References Cited

U.S. PATENT DOCUMENTS

| | | |
|---|---|---|
| 4,762,130 A | 8/1988 | Fogarty et al. |
| 4,902,508 A | 2/1990 | Badylak et al. |
| 5,129,910 A | 7/1992 | Phan et al. |
| 5,197,976 A | 3/1993 | Herweck et al. |
| 5,413,601 A | 5/1995 | Keshelava |
| 5,522,880 A | 6/1996 | Barone et al. |
| 5,562,724 A | 10/1996 | Vorwerk et al. |
| 5,571,173 A | 11/1996 | Parodi |
| 5,578,071 A | 11/1996 | Parodi |
| 5,591,229 A | 1/1997 | Parodi |
| 5,617,878 A | 4/1997 | Taheri |
| 5,653,743 A | 8/1997 | Martin |
| 5,693,087 A | 12/1997 | Parodi |
| 5,711,969 A | 1/1998 | Patel et al. |
| 5,733,337 A | 3/1998 | Carr, Jr. et al. |
| 5,824,040 A | 10/1998 | Cox et al. |
| 5,885,619 A | 3/1999 | Patel et al. |
| 5,921,995 A | 7/1999 | Kleshinski |
| 5,955,110 A | 9/1999 | Patel et al. |
| 5,968,096 A | 10/1999 | Whitson et al. |
| 5,984,955 A | 11/1999 | Wisselink |
| 5,993,481 A | 11/1999 | Marcade et al. |
| 6,030,414 A | 2/2000 | Taheri |
| 6,039,754 A | 3/2000 | Caro |
| 6,059,824 A | 5/2000 | Taheri |
| 6,077,296 A | 6/2000 | Shokoohi et al. |
| 6,093,203 A | 7/2000 | Uflacker |
| 6,099,558 A | 8/2000 | White et al. |
| 6,102,940 A | 8/2000 | Robichon et al. |
| 6,136,022 A | 10/2000 | Nuñez et al. |
| 6,152,956 A | 11/2000 | Pierce |
| 6,187,033 B1 | 2/2001 | Schmitt et al. |
| RE37,107 E | 3/2001 | Wells-Roth |
| 6,206,931 B1 | 3/2001 | Cook et al. |
| 6,210,429 B1 | 4/2001 | Vardi et al. |
| 6,221,090 B1 | 4/2001 | Wilson |
| 6,221,098 B1 | 4/2001 | Wilson et al. |
| 6,264,682 B1 | 7/2001 | Wilson et al. |
| 6,283,991 B1 | 9/2001 | Cox et al. |
| 6,290,731 B1 | 9/2001 | Solovay et al. |
| 6,325,819 B1 | 12/2001 | Pavenik et al. |
| 6,325,826 B1 | 12/2001 | Vardi et al. |
| 6,334,869 B1 | 1/2002 | Leonhardt et al. |
| 6,344,056 B1 | 2/2002 | Dehdashtian |
| 6,358,284 B1 | 3/2002 | Fearnot et al. |
| 6,361,544 B1 | 3/2002 | Wilson et al. |
| 6,395,018 B1 | 5/2002 | Castaneda |
| 6,409,750 B1 | 6/2002 | Heyodoh et al. |
| 6,409,756 B1 | 6/2002 | Murphy |
| 6,409,757 B1 | 6/2002 | Trout, III et al. |
| 6,428,565 B1 | 8/2002 | Wisselink |
| 6,478,817 B2 | 11/2002 | Schmitt et al. |
| 6,482,227 B1 | 11/2002 | Solovay |
| 6,508,836 B2 | 1/2003 | Wilson et al. |
| 6,517,574 B1 | 2/2003 | Chuter |
| 6,520,988 B1 | 2/2003 | Colombo et al. |
| 6,524,335 B1 | 2/2003 | Hartley et al. |
| 6,554,856 B1 | 4/2003 | Doorly et al. |
| 6,579,309 B1 | 6/2003 | Loos et al. |
| 6,582,394 B1 | 6/2003 | Reiss et al. |
| 6,585,758 B1 | 7/2003 | Chouinard et al. |
| 6,599,302 B2 | 7/2003 | Houser et al. |
| 6,599,315 B2 | 7/2003 | Wilson |
| 6,641,606 B2 | 11/2003 | Ouriel et al. |
| 6,645,242 B1 | 11/2003 | Quinn |
| 6,652,567 B1 | 11/2003 | Deaton |
| 6,663,667 B2 | 12/2003 | Dehdashtian et al. |
| 6,669,720 B1 | 12/2003 | Pierce |
| 6,706,062 B2 | 3/2004 | Vardi et al. |
| 6,723,116 B2 | 4/2004 | Taheri |
| 6,733,522 B2 | 5/2004 | Schmitt et al. |
| 6,733,523 B2 | 5/2004 | Shaolian et al. |
| 6,767,358 B2 | 7/2004 | Leonhardt et al. |
| 6,773,457 B2 | 8/2004 | Ivancev et al. |
| 7,105,020 B2 | 9/2006 | Greenberg et al. |
| 7,232,459 B2 | 6/2007 | Greenberg et al. |
| 8,012,193 B2 | 9/2011 | Hartley et al. |
| 8,845,708 B2 | 9/2014 | Hartley et al. |
| 2001/0012962 A1 | 8/2001 | Schmitt et al. |
| 2001/0027338 A1 | 10/2001 | Greenberg |
| 2001/0037142 A1 | 11/2001 | Stelter et al. |
| 2002/0052648 A1 | 5/2002 | McGuckin, Jr. et al. |
| 2002/0058984 A1 | 5/2002 | Butaric et al. |
| 2002/0058986 A1 | 5/2002 | Landau et al. |
| 2002/0058987 A1 | 5/2002 | Butaric et al. |
| 2002/0058991 A1 | 5/2002 | Schmitt |
| 2002/0058993 A1 | 5/2002 | Landau et al. |
| 2002/0082684 A1 | 6/2002 | Mishaly |
| 2002/0099441 A1 | 7/2002 | Dehdashtian |
| 2002/0111674 A1 | 8/2002 | Chouinard et al. |
| 2002/0120327 A1 | 8/2002 | Cox et al. |
| 2002/0143383 A1 | 10/2002 | Parodi |
| 2002/0144696 A1 | 10/2002 | Sharkawy et al. |
| 2002/0151957 A1 | 10/2002 | Kerr |
| 2002/0156517 A1 | 10/2002 | Perouse |
| 2002/0156522 A1 | 10/2002 | Ivancev et al. |
| 2002/0169497 A1 | 11/2002 | Wholey et al. |
| 2002/0173840 A1 | 11/2002 | Brucker et al. |
| 2002/0193872 A1 | 12/2002 | Trout, III et al. |
| 2002/0198585 A1 | 12/2002 | Wisselink |
| 2003/0009212 A1 | 1/2003 | Kerr |
| 2003/0033005 A1 | 2/2003 | Houser et al. |
| 2003/0074050 A1 | 4/2003 | Kerr |
| 2003/0093145 A1 | 5/2003 | Lawrence-Brown et al. |
| 2003/0120333 A1 | 6/2003 | Ouriel et al. |
| 2003/0130720 A1 | 7/2003 | De Palma et al. |
| 2003/0130724 A1 | 7/2003 | De Palma et al. |
| 2003/0195614 A1 | 10/2003 | Ryan et al. |
| 2003/0199967 A1 | 10/2003 | Hartley et al. |
| 2003/0199973 A1 | 10/2003 | Chuter et al. |
| 2003/0204242 A1 | 10/2003 | Zarins et al. |
| 2003/0204243 A1 | 10/2003 | Shiu |
| 2003/0220682 A1 | 11/2003 | Kujawski |
| 2003/0225453 A1 | 12/2003 | Murch |
| 2004/0034406 A1 | 2/2004 | Thramann |
| 2004/0044396 A1 | 3/2004 | Clerc et al. |
| 2004/0059406 A1 | 3/2004 | Cully et al. |
| 2004/0073288 A1 | 4/2004 | Kerr |
| 2004/0093078 A1 | 5/2004 | Moll et al. |
| 2004/0106972 A1 | 6/2004 | Deaton |
| 2004/0133266 A1 | 7/2004 | Clerc et al. |
| 2004/0138737 A1 | 7/2004 | Davidons et al. |
| 2004/0167607 A1 | 8/2004 | Frantzen |
| 2004/0193245 A1 | 9/2004 | Deem et al. |
| 2004/0193254 A1 | 9/2004 | Greenberg et al. |

(56) References Cited

U.S. PATENT DOCUMENTS

| | | |
|---|---|---|
| 2005/0059923 A1 | 3/2005 | Gamboa |
| 2005/0102021 A1 | 5/2005 | Osborne |
| 2005/0131517 A1 | 6/2005 | Hartley et al. |
| 2005/0131519 A1 | 6/2005 | Hartley |
| 2005/0131525 A1 | 6/2005 | Hartley |
| 2005/0182476 A1* | 8/2005 | Hartley ............... A61F 2/07 623/1.11 |
| 2005/0273155 A1 | 12/2005 | Bahler et al. |
| 2006/0004433 A1 | 1/2006 | Greenberg et al. |
| 2006/0095118 A1 | 5/2006 | Hartley |
| 2006/0136046 A1 | 6/2006 | Hartley et al. |
| 2006/0247761 A1 | 11/2006 | Greenberg et al. |
| 2007/0055346 A1 | 3/2007 | Chu et al. |
| 2007/0142896 A1 | 6/2007 | Anderson et al. |
| 2007/0219614 A1* | 9/2007 | Hartley ............... A61F 2/07 623/1.11 |
| 2007/0250154 A1* | 10/2007 | Greenberg ............... A61F 2/07 623/1.13 |
| 2007/0299499 A1* | 12/2007 | Hartley ............... A61F 2/962 623/1.11 |
| 2008/0109065 A1* | 5/2008 | Bowe ............... A61F 2/95 623/1.13 |
| 2009/0043377 A1 | 2/2009 | Greenberg et al. |
| 2010/0161025 A1* | 6/2010 | Kuppurathanam ....... A61F 2/07 623/1.13 |
| 2010/0198328 A1* | 8/2010 | Hartley ............... A61F 2/95 623/1.11 |
| 2011/0307048 A1* | 12/2011 | Ivancev ............... A61F 2/07 623/1.11 |
| 2012/0221094 A1* | 8/2012 | Cunningham ............ A61F 2/07 623/1.12 |
| 2014/0148888 A1* | 5/2014 | Barrand ............... A61F 2/856 623/1.2 |
| 2014/0257464 A1* | 9/2014 | Roeder ............... A61F 2/856 623/1.35 |
| 2014/0371838 A1* | 12/2014 | Buddery ............... A61F 2/07 623/1.11 |

FOREIGN PATENT DOCUMENTS

| | | |
|---|---|---|
| EP | 0 903 118 A2 | 9/1994 |
| EP | 0 903 118 A3 | 9/1994 |
| JP | 04-231954 A | 8/1992 |
| JP | 07-008512 A | 1/1995 |
| JP | 2000-279532 | 10/2000 |
| JP | 2001-503285 | 3/2001 |
| WO | WO 95/09585 A1 | 4/1995 |
| WO | WO 95/16406 A1 | 6/1995 |
| WO | WO 95/21592 A1 | 8/1995 |
| WO | WO 97/33532 A2 | 9/1997 |
| WO | WO 98/22158 A2 | 5/1998 |
| WO | WO 98/22158 A3 | 5/1998 |
| WO | WO 98/53761 A1 | 12/1998 |
| WO | WO 99/13808 A1 | 3/1999 |
| WO | WO 99/48441 A1 | 9/1999 |
| WO | WO 00/32241 A1 | 6/2000 |
| WO | WO 02/067815 A1 | 9/2002 |
| WO | WO 03/065933 A1 | 8/2003 |
| WO | WO 03/082153 A2 | 10/2003 |
| WO | WO 03/082153 A3 | 10/2003 |
| WO | WO 2004/064686 A1 | 8/2004 |
| WO | WO 2004/089249 | 10/2004 |
| WO | WO 2004/093746 A1 | 11/2004 |
| WO | WO 2006/113501 A1 | 10/2006 |

OTHER PUBLICATIONS

Greenberg et al., "Endovascular Management of Juxtarenal Aneurysms with Fenestrated Endovascular Grafting," 39 Journal of Vascular Surgery, No. 2, pp. 279-287 (Feb. 2004).

Greenberg et al., "Primary Endovascular Repair of Juxtarenal Aneurysms with Fenestrated Endovascular Grafting," 27 European Journal of Vascular Surgery, pp. 484-491 (2004).

Huynh et al., "Remodeling of an Acellular Collagen Graft into a Physiologically Responsive Neovessel," 17 Nature Biotechnology, pp. 1083-1086 (Nov. 1999).

Examiner's First Report for Australian Application No. 2007240703, dated Aug. 30, 2011, 3 pages.

Patent Examination Report No. 1 for Australian Application No. 2011250798, dated Jun. 27, 2012, 4 pages.

Patent Examination Report No. 1 for Australian Application No. 2011250799, dated Jul. 20, 2012, 4 pages.

Office Action and English translation for Chinese Application No. 200780022712.1, dated Aug. 2, 2010, 8 pages.

Examination for EP 07755802.1 dated Dec. 28, 2011, 4 pages.

Communication pursuant to Article 96(2) EPC, dated Sep. 17, 2007, for related European Application No. 04 701 753.8-2310.

Examination Report for corresponding EP Application No. 07755802.1, dated Feb. 16, 2017, 4 pages.

Office Action and English translation for Japanese Application No. 2012-178429 dated Aug. 27, 2013, 7 pages.

Office Action and English translation for Japanese Application No. 2012-178429 dated Jun. 3, 2014, 4 pages.

International Search Report and Written Opinion of the International Searching Authority for International Application No. PCT/US2009/004124, dated Sep. 30, 2009, 15 pages.

Office Action from co-pending U.S. Appl. No. 12/174,451, dated Jan. 20, 2010, 6 pages.

Office Action from co-pending U.S. Appl. No. 12/174,451, dated Jul. 9, 2010, 8 pages.

* cited by examiner

TWIN BIFURCATED STENT GRAFT

RELATED APPLICATIONS

This application is a continuation of U.S. application Ser. No. 11/788,285, filed Apr. 19, 2007, which claims the benefit of the filing date under 35 U.S.C. § 119(e) of Provisional U.S. Patent Application Ser. No. 60/793,282, filed Apr. 19, 2006. All of the foregoing applications are hereby incorporated by reference.

INCORPORATION BY REFERENCE

The following co-pending patent applications are referred to in the following description:
- U.S. patent application Ser. No. 10/962,763 entitled "Introducer for Iliac Side Branch Device"
- PCT Patent Publication No. WO 98/53761 entitled "A Prosthesis and a Method of Deploying a Prosthesis"
- U.S. patent application Ser. No. 11/600,655 entitled "Stent Graft Introducer"

The entire content of each of these applications is hereby incorporated by reference. As disclosed in U.S. Publication No. 2005/0182476, an introducer as shown in the figures has an introducer catheter 3 extending over a guide wire catheter 5. The guide wire catheter 5 extends from the distal end 7 of the introducer 1 to immediately distal of the nose cone dilator 11. A branched stent graft 13 is retained at its proximal end by a retention arrangement (see FIGS. 12 and 13 for one example of a proximal retention arrangement) onto the introducer immediately distal of the nose cone dilator 11. The branched stent graft 13 is retained at its distal end by another retention arrangement (see FIGS. 14 and 15 for examples of a proximal retention arrangement) onto the introducer. A sleeve 15 operated by a sleeve manipulator 17 is mounted on the introducer catheter 3 and in the ready to deploy position the sleeve 15 extends over the branched stent graft 13 to the nose cone dilator 11. As illustrated in FIG. 7, however, the sleeve 15 is withdrawn so that the branched stent graft is exposed to show detail of the assembly. A handle 19 at the distal end of the introducer catheter 3 enables manipulation of the introducer 1.

BACKGROUND

This invention relates to a medical device and more particularly a device which can be deployed by endovascular means into the vasculature of a patient.

BRIEF SUMMARY

There have been proposed bifurcated endovascular devices which can be deployed into the vasculature, particularly in the region of the aortic bifurcation, so that an aneurysm in the aorta can be bridged by placement of the endovascular device with a proximal portion which seals into a non-aneurysed portion of the aorta adjacent to the renal arteries, a first leg which extends down one iliac artery to a non-aneurysed portion of the iliac artery and another short leg into which a leg extension may be placed to extend into a non-aneurysed portion of the contra-lateral iliac artery.

There can be problems, however, if the aneurysm of the aorta extends down into one or other of the iliac arteries. Each of the common iliac arteries branches into the internal and external iliac arteries and it is necessary in such a situation that a blood flow path can be directed through an endovascular stent graft into each of these arteries.

The object of this invention is to provide a single endovascularly deployed medical device which can solve this problem or at least provide a physician with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

DESCRIPTION OF THE INVENTION

In one form therefore the invention is said to reside in a stent graft comprising a tubular body of a biocompatible graft material defining a main lumen therethrough, a bifurcation in the tubular body at one end thereof and a first leg and a second leg extending from the bifurcation, the first leg being a long leg and the second leg being a short leg, the first and second legs having respective first and second lumens therethrough and the first and second lumens being in fluid communication with the main lumen, characterised by the first long leg comprising a side arm with a side arm lumen therethrough and the side arm lumen being in fluid communication with the first leg lumen, whereby the stent graft can be deployed into the vasculature of a patient with the tubular body being in an aorta of the patient, the first leg extending down an iliac artery, the second leg being directed towards a contralateral iliac artery and the side arm on the first leg directed to an internal artery of the iliac artery.

In one preferred embodiment the side arm comprises a tube of corrugated biocompatible graft material and the tube extends part helically around the first leg.

In an alternative embodiment the side arm comprises a tube of biocompatible graft material and at least one self expanding stent on the tube of biocompatible graft material. Co-pending United States Patent Application Serial No. entitled " "discloses side arm tubes suitable for the present invention.

Preferably the first leg includes an aperture or fenestration proximally of the side arm and a valve arrangement to prevent fluid flow through the aperture from inside of the leg to outside of the leg.

Preferably the aperture includes a resilient reinforcement ring around the aperture.

The valve arrangement can comprise a sleeve of a biocompatible graft material within the first leg and a self expanding stent within the sleeve, the sleeve being fastened at its proximal end to the first leg proximal of the aperture and the self expanding stent being fastened to the sleeve, whereby the self expanding stent forces the sleeve against the inner surface of the first leg around the aperture to prevent fluid flow through the aperture from inside of the leg to outside of the leg.

In one preferred embodiment the sleeve of a biocompatible graft material comprises a cylindrical form. In an alternative embodiment the sleeve of a biocompatible graft material comprises a semi-cylindrical form.

Alternatively the valve can be formed from a self expanding stent to which a part cylindrical portion of biocompatible graft material is stitched along spaced apart struts of the self expanding stent. These two components together can form a valve assembly which can be stitched into the longer leg of the stent graft.

The valve assembly can further include a semi-circular resilient wire around the distal end of the part cylindrical portion of biocompatible graft material forming the valve member. This semi-circular resilient wire around the distal end of the part cylindrical portion of biocompatible graft material will assist with sealing off the fenestration by ensuring that the distal end of the valve member is held against the inside of the wall of the longer first leg of the stent graft.

The biocompatible graft material can include polytetrafluoroethylene, Dacron, polyamide or any other suitable biocompatible graft material.

While Dacron, expanded polytetrafluoroethylene (ePTFE), or other synthetic biocompatible materials can be used for the tubular graft material for the stent graft, a naturally occurring biomaterial, such as collagen, is highly desirable, particularly a specially derived collagen material known as an extracellular matrix (ECM), such as small intestinal submucosa (SIS). Besides SIS, examples of ECM's include pericardium, stomach submucosa, liver basement membrane, urinary bladder submucosa, tissue mucosa, and dura mater.

SIS is particularly useful, and can be made in the fashion described in Badylak et al., U.S. Pat. No. 4,902,508; Intestinal Collagen Layer described in U.S. Pat. No. 5,733,337 to Carr and in 17 Nature Biotechnology 1083 (Nov. 1999); Cook et al., WIPO Publication WO 98/22158, dated 28 May 1998, which is the published application of PCT/US97/14855, the teachings of which are incorporated herein by reference. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. In addition to xenogenic biomaterials, such as SIS, autologous tissue can be harvested as well, for use in forming the tubular graft material. Additionally Elastin or Elastin-Like Polypetides (ELPs) and the like offer potential as a material to fabricate the tubular graft material to form a device with exceptional biocompatibility.

SIS is available from Cook Biotech, West Lafayette, Ind., USA.

It will be seen that by this invention there is provided a stent graft which has a main bifurcation to allow access into each of the iliac arteries and in one of the legs extending from the bifurcation there is a further bifurcation or branch which will enable access into the internal iliac artery. There is some advantage in having a double or twin bifurcation stent graft.

As discussed above there is preferably a valve arrangement proximal of the side arm or side branch of the iliac leg of the bifurcated stent graft. The valve allows an indwelling catheter to be provided through the sidearm in the iliac artery at the time of deployment to assist with deployment of leg extension into the internal iliac artery.

U.S. patent application Ser. No. 10/962,763 entitled "Introducer for Iliac Side Branch Device" discloses an arrangement for using an indwelling catheter to access an internal iliac artery and the teaching of this specification is incorporated herewith in its entirety.

In this case the indwelling catheter can be extended and its guide wire snared from the contra-lateral artery and the leg extension placed into the internal iliac artery before the leg extension is placed into the iliac artery.

In a further form the invention is said to reside in a stent graft comprising a tubular body of a biocompatible graft material defining a main lumen therethrough an aperture defining a fenestration in the tubular body and a valve arrangement to prevent fluid flow through the aperture.

Preferably the aperture includes a resilient reinforcement ring around the aperture.

Preferably the valve arrangement comprises a sleeve of a biocompatible graft material within the tubular body and a self expanding stent within the sleeve, the sleeve being fastened at its proximal end to the first leg proximal of the aperture and the self expanding stent being fastened to the sleeve, whereby the self expanding stent forces the sleeve against the inner surface of the tubular body around the aperture to prevent fluid flow through the aperture.

The sleeve of a biocompatible graft material can comprise a cylindrical form or alternatively a semi-cylindrical form.

In one embodiment the valve arrangement comprises a valve assembly comprising a self expanding stent to which a part cylindrical portion of biocompatible graft material is stitched along spaced apart struts of the self expanding stent.

The valve assembly can further comprise a semi-circular resilient wire around the distal end of the part cylindrical portion of biocompatible graft material forming the valve member.

This then generally describes the invention but to assist with understanding reference will now be made to the accompanying drawings which show further embodiments of the invention.

DETAILED DESCRIPTION OF THE DRAWINGS AND THE PRESENTLY PREFERRED EMBODIMENTS

Figure 1:
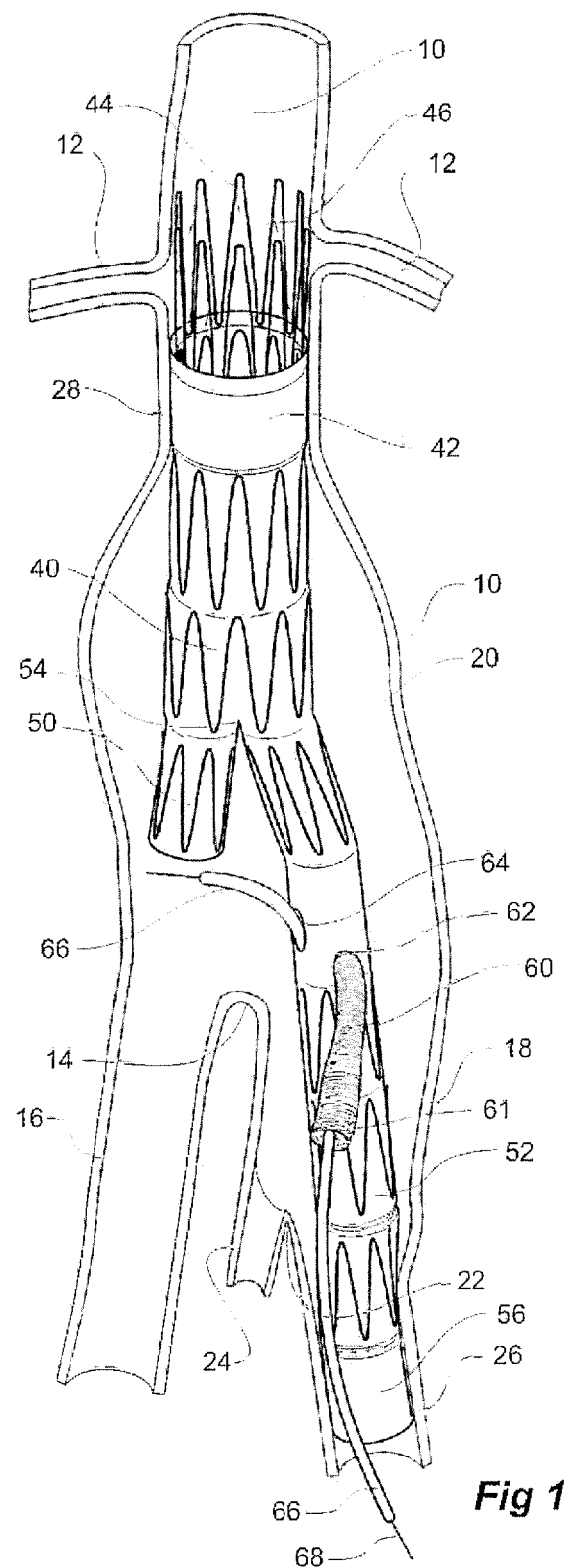
FIG. 1 shows a first embodiment of stent graft according to the invention as it would be deployed into the vasculature before placement of an iliac side branch.
Figure 2:
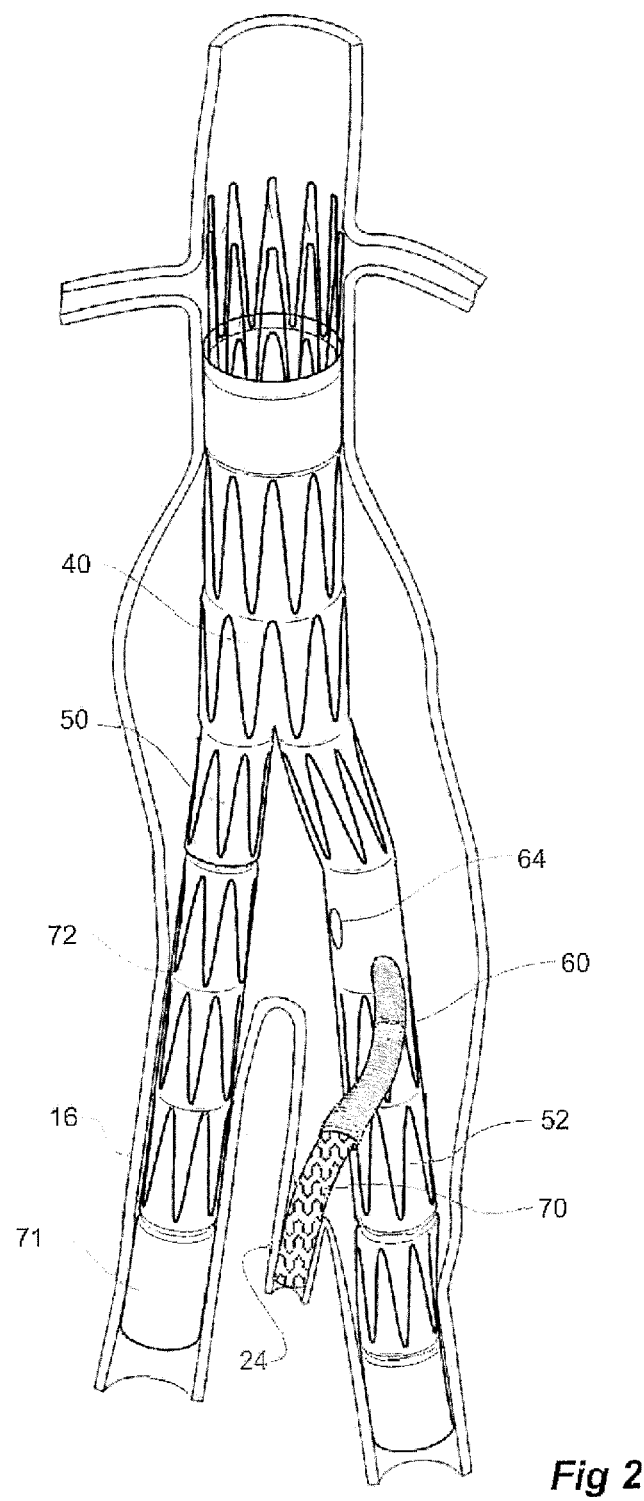
FIG. 2 shows the embodiment of FIG. 1 with the side branch installed into the internal iliac artery and the leg extension in the contralateral iliac artery.

Looking more closely at the drawings and in particular FIGS. 1 and 2 it will be seen that a schematic view of part of the vascular arrangement of a patient is illustrated incorporating a stent graft according to the present invention.

The vasculature comprises an aorta 10 in the region between the renal arteries 12 and the aortic bifurcation 14. Common iliac arteries 16 and 18 extend down from the aortic bifurcation 14. The aorta 10 has an aneurysm 20 which extends down into the common iliac artery 18 as far as the bifurcation 22 between the internal iliac artery 24 and the external iliac artery 26.

To traverse the aneurysm 20 a twin bifurcated aortic stent graft 40 according to one embodiment of the present invention has been deployed into the aorta 10. In this drawing the introduction device which is used to deploy the stent graft into the vasculature has been omitted to assist clarity. In our earlier patent application, PCT Patent Publication No. WO 98/53761 entitled "A prosthesis and a method deploying a prosthesis" there is disclosed an introducer for a stent graft which is suitable for use with the present invention. The proximal end 42 of the bifurcated stent graft 40 is engaged into non-aneurysed portion 28 of the aorta 10 just distal of the renal arteries 12. In this embodiment stent graft 40 has a proximally extending supra-renal exposed stent 44 with barbs 46 engaging the wall of the aorta proximal of the renal arteries to provide a secure position to prevent migration of the stent graft. The stent graft 40 has a short leg 50 and a long leg 52 extending from the graft bifurcation 54. The longer leg 52 has a sealing surface 56 at its distal end which engages into a non-aneurysed portion of the external iliac artery 26.

The longer leg 52 has a side arm 60 which in this embodiment is in the form of a corrugated tube extending in a part helical manner from its connection at a fenestration 62 into the longer leg 52. The side arm 60 extends in a distal direction and helically partly around the longer leg 52 and has a distal end 61 remote from its connection with the longer leg 52 which opens adjacent to the internal iliac artery 24.

A fenestration 64 is placed into the longer leg 52 proximal of the connection of the side arm 60 into the longer leg 52. The fenestration 64 has a valve arrangement within it to close it off as will be discussed with reference to FIGS. 3 to 5.

During deployment of the stent graft into the vasculature of a patient an in-dwelling catheter 66 extends through the side arm 60 and out through the valved fenestration 64. The indwelling catheter includes a guide wire 68.

FIG. 2 shows the embodiment of FIG. 1 but after deployment of an extension piece 70 into the corrugated side arm 60 and deployment of a leg extension 72 into the short leg 50 of the bifurcated stent graft 40 which seals into a non-aneurysed portion of the iliac artery 16. U.S. patent application Ser. No. 10/962,763 entitled "Introducer for Iliac Side Branch Device" discloses an arrangement for using an indwelling catheter to access an internal iliac artery. At this stage the indwelling catheter has been withdrawn and the fenestration 64 is closed off by the valve arrangement.

The extension piece 70 seals into a non-aneurysed portion of the internal iliac artery 24.

The process of deployment of a stent graft according to this embodiment of the invention will be discussed with reference to FIGS. 15A to 15M.

Figure 3:
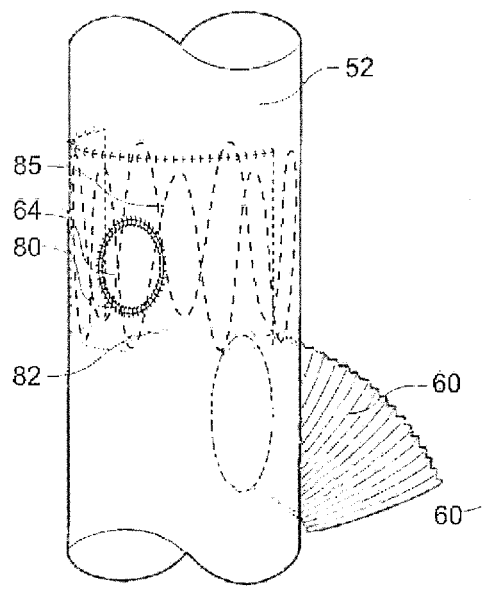
FIG. 3 shows a schematic view of part of the leg of the stent graft of the present invention in particular showing one embodiment of the valve arrangement.
Figure 4:
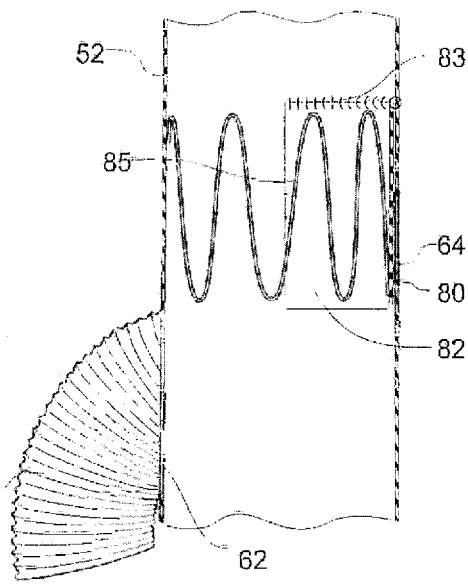
FIG. 4 shows a cross-section of embodiment shown in FIG. 3.
Figure 5:
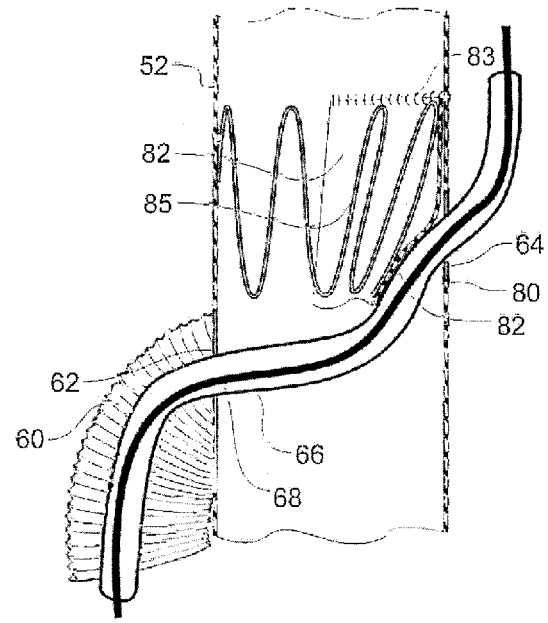
FIG. 5 shows a same view as FIG. 4 except with the indwelling catheter extending through the corrugated side arm and valve.

FIGS. 3, 4 and 5 show a first embodiment of valve arrangement suitable for the present invention.

In this embodiment the longer leg 52 of the bifurcated stent graft 40 as shown in FIG. 1 has a fenestration 64 defined by a peripheral resilient ring 80 which is stitched into the tube of the longer leg 52. Inside the longer leg is a semi-circular portion of biocompatible graft material 82 and a resilient self-expanding zigzag stent 85 which engages with the semi-circular biocompatible graft material 82 and engages it against the inside wall of the longer leg 52 and in particular over the fenestration 64. By this arrangement the fenestration 64 is held in a closed configuration. The semi-circular piece 82 is stitched by stitching 83 at its proximal end to the inner wall of the longer leg 52.

Substantially opposite to the fenestration 64 in the tubular longer leg 52 the side arm 60 extends from a fenestration 62 in the tubular longer leg 52.

FIG. 5 shows the embodiment as shown in FIG. 4 except that an indwelling catheter 66 and guide wire 68 through the indwelling catheter extend through the side arm 60 and through the fenestration 64 and this lifts the valve 82 off the fenestration 64 against the restoring force of the resilient self expanding stent 85.

Figure 6:
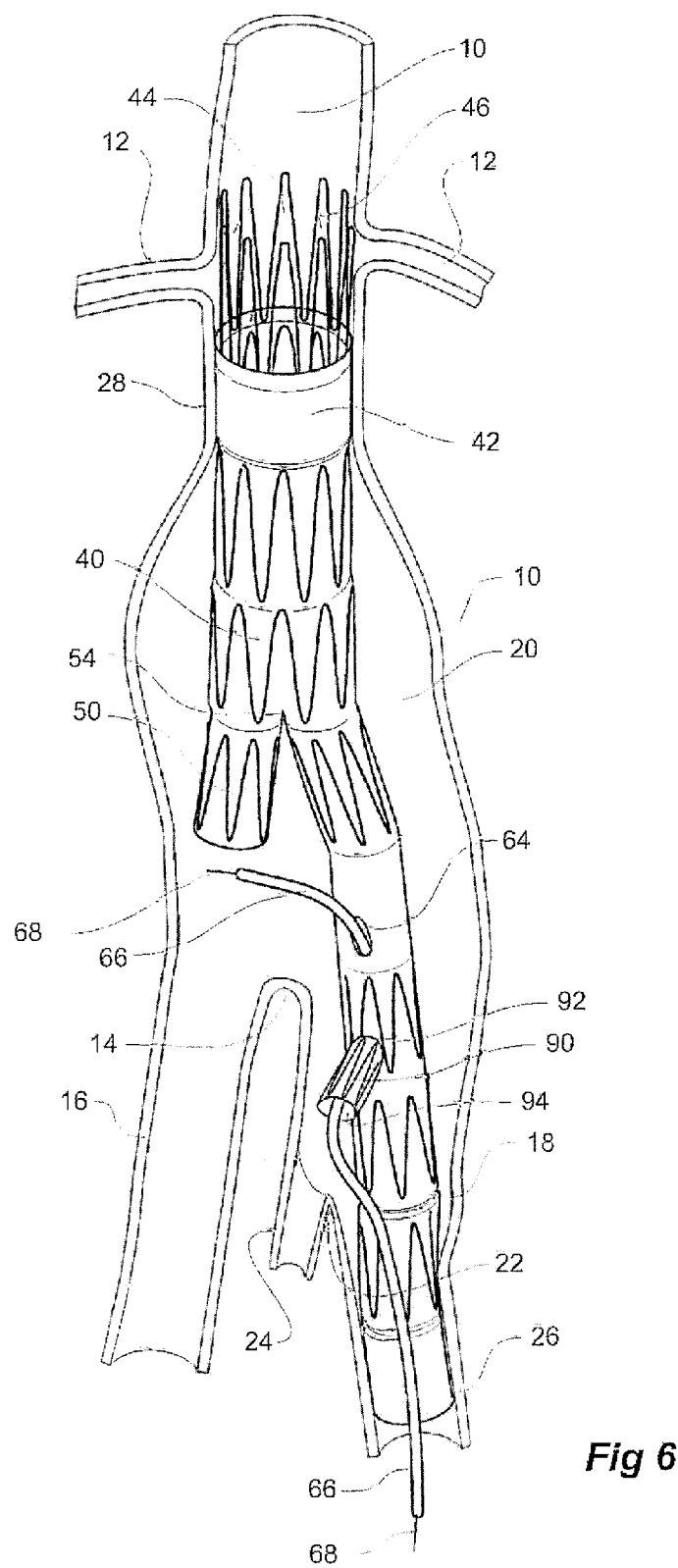
FIG. 6 shows an alternative embodiment of stent graft deployed into a schematic vasculature with an alternative arrangement of side arm.
Figure 7:
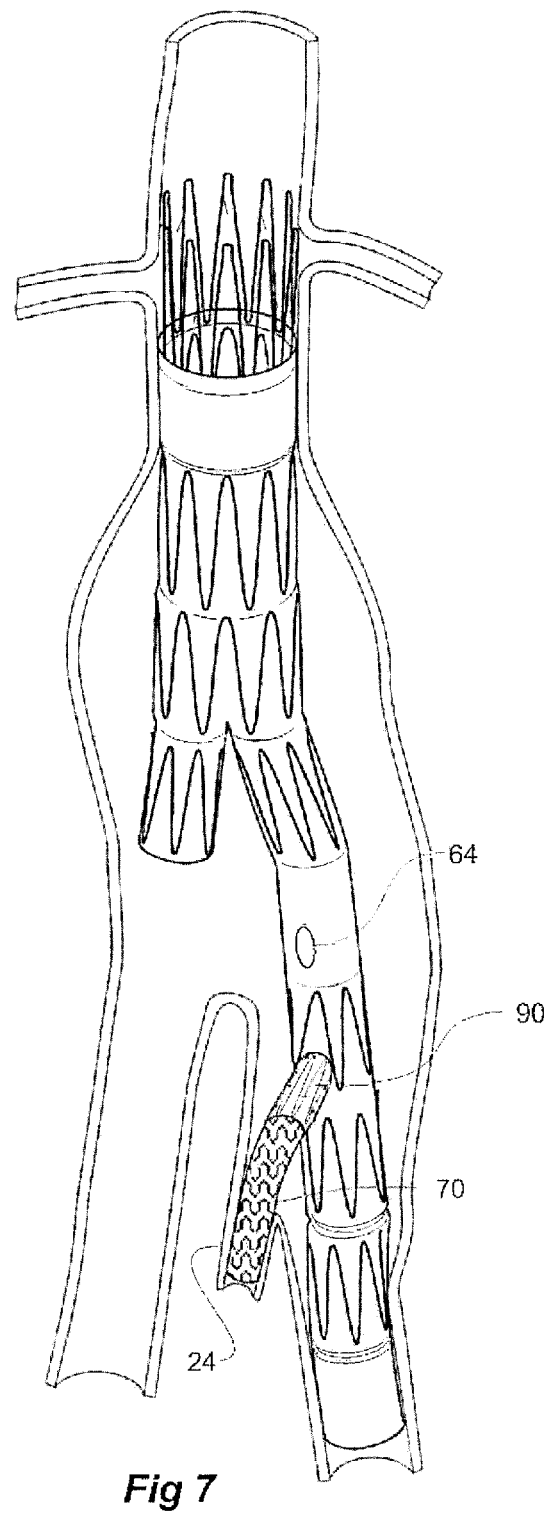
FIG. 7 shows embodiment of FIG. 6 at the stage where the indwelling catheter has been snared and pulled down the contralateral artery and the indwelling catheter has been used to deploy an extension piece into internal iliac artery.

FIGS. 6 and 7 show an alternative embodiment of bifurcated stent graft according to the present invention in the vasculature of a patient. The vasculature and the bifurcated stent graft are similar to the earlier embodiment shown in FIGS. 1 and 2 and the same reference numerals are used for corresponding items.

The vasculature comprises an aorta 10 in the region between the renal arteries 12 and the aortic bifurcation 14. Common iliac arteries 16 and 18 extend down from the aortic bifurcation. The aorta 10 has an aneurysm 20 which extends down into the common iliac artery 18 so far as the bifurcation 22 between the internal iliac artery 24 and external iliac artery 26.

To traverse the aneurysm a bifurcated aortic stent graft 40 has been deployed into the aorta 10. The proximal end 42 of the bifurcated stent graft 40 is engaged into non-aneurysed portion 28 of the aorta 10 just distal of the renal arteries 12. In this embodiment stent graft 40 has a proximally extending supra-renal exposed stent 44 with barbs 46 engaging the wall of the aorta proximal of the renal arteries to provide a secure position to prevent migration of the stent graft. The stent graft 40 has a short leg 50 and a long leg 52 extending from the graft bifurcation 54. The longer leg 52 has a sealing surface 56 at its distal end which engages into a non-aneurysed portion of the external iliac artery 26.

The longer leg 52 has a side arm 90 which in this embodiment is in the form of a stented tube extending from a fenestration 92 in the longer leg 52. The side arm 90 extends in a distal direction and has an end 94 remote from its connection with the longer leg 52 which opens adjacent to the internal iliac artery 24.

A fenestration 64 is placed into the longer leg 52 proximal of the connection of the side arm 90 into the longer leg 52.

The fenestration 64 has a valve arrangement within it to close it off as will be discussed with reference to FIGS. 8 to 10.

During deployment of the stent graft into the vasculature of a patient an in-dwelling catheter 66 extends through the side arm 90 and out through the valved fenestration 64. The indwelling catheter includes a guide wire 68 therethrough.

FIG. 7 shows the embodiment of FIG. 6 but after deployment of an extension piece 70 into the side arm 90. U.S. patent application Ser. No. 10/962,763 entitled "Introducer for Iliac Side Branch Device" discloses an arrangement for using an indwelling catheter to access an internal iliac artery. At this stage the indwelling catheter has been withdrawn and the fenestration 64 is closed off by the valve arrangement. The extension piece 70 seals into a non-aneurysed portion of the internal iliac artery 24.

Figure 8:
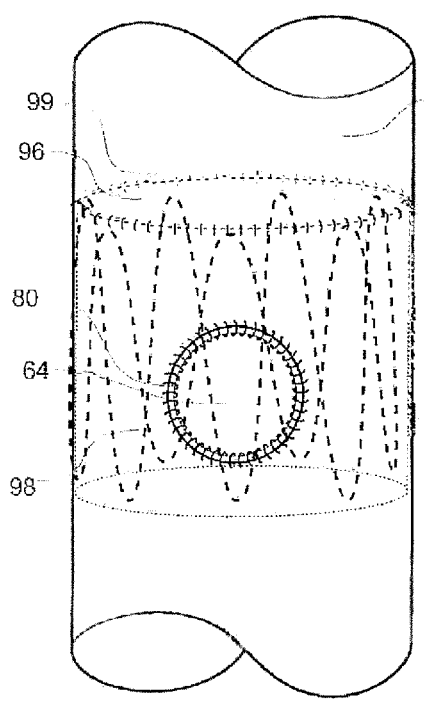
FIG. 8 shows an alternative embodiment of valve arrangement suitable for the embodiment of stent graft shown in FIGS. 6 and 7.
Figure 9:
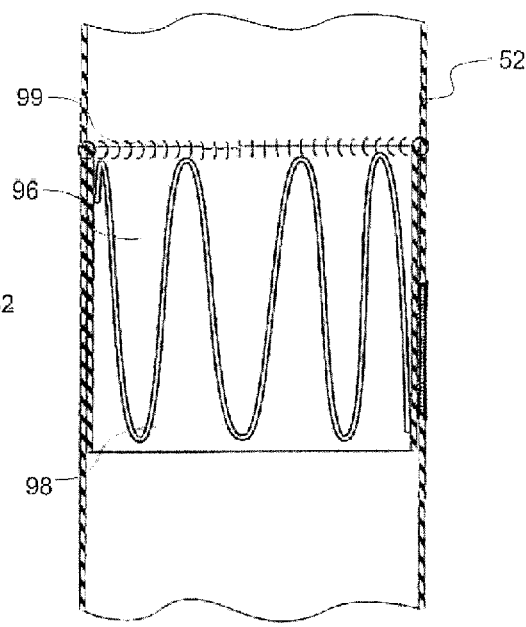
FIG. 9 shown a cross-section thought the valve arrangement of FIG. 8.
Figure 10:
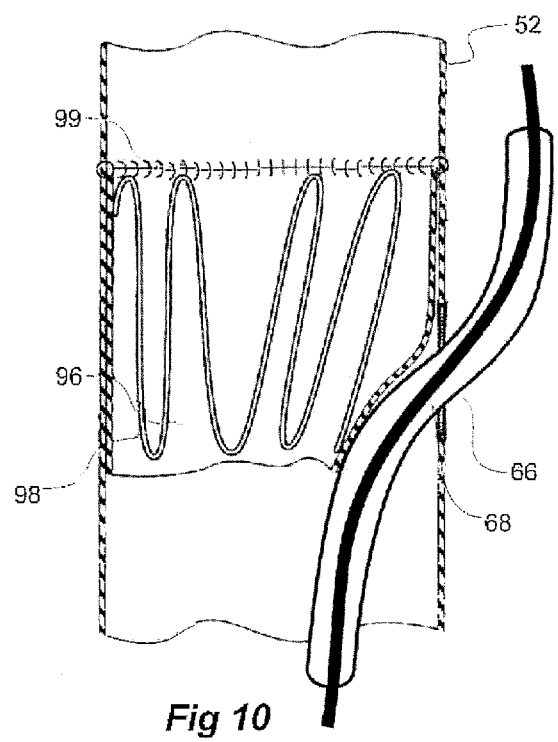
FIG. 10 shows the valve arrangement of FIGS. 8 and 9 with an indwelling catheter extending through it.
Figure 11:
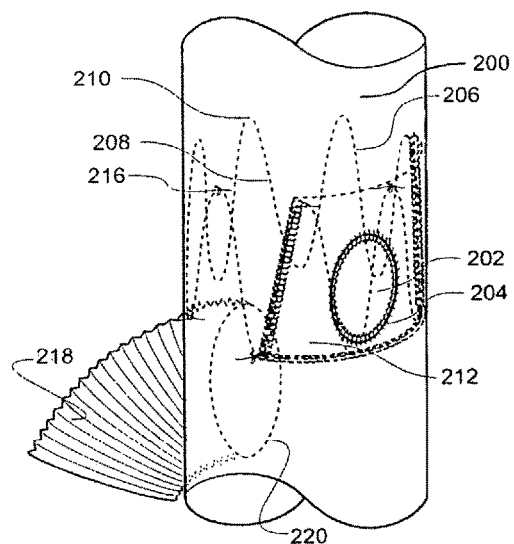
FIG. 11 shows an alternative embodiment of valve arrangement suitable for the embodiment of stent graft shown in FIGS. 6 and 7.

FIGS. 8, 9 and 10 show an alternative embodiment of valve arrangement suitable for the present invention.

In this embodiment of valve the longer leg 52 of the bifurcated stent graft 40 as shown in FIG. 6 has a fenestration 64 defined by a peripheral resilient ring 80 which is stitched into the tubular wall of the longer leg 52. Inside the longer leg is a cylindrical portion of biocompatible graft material 96 and a self-expanding zigzag stent 98 which engages with the cylindrical biocompatible graft material 96 and engages it against the inside wall of the longer leg 52 and in particular over the fenestration 64. By this arrangement the fenestration 64 is held in a closed configuration. The cylindrical portion of biocompatible graft material 96 is stitched by stitching 99 at its proximal end to the inner wall of the longer leg 52.

FIG. 10 shows the embodiment as shown in FIG. 9 except that an indwelling catheter 66 and guide wire 68 through the catheter extend through the side arm 60 and through the fenestration 64 and this lifts the valve 96 for the fenestration 64.

FIGS. 11 to 14 show a further embodiment of valve arrangement suitable for the present invention.

Figure 12:
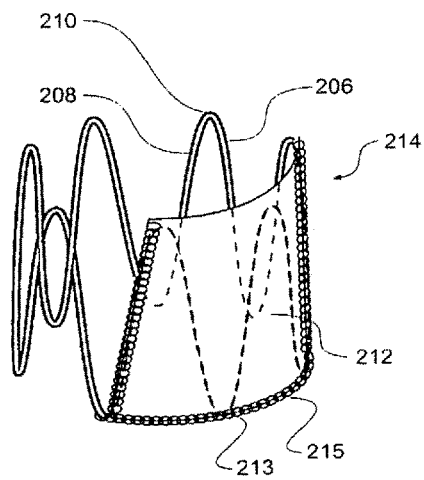
FIG. 12 shown a detail of the valve arrangement of FIG. 11 showing the self expanding stent with a valve member mounted onto it.

In this embodiment the longer leg 200 of the bifurcated stent graft 40 (FIG. 1) has a fenestration 202 defined by a peripheral resilient ring 204 which is stitched into the tube of the longer leg 200. Inside the longer leg is a self expanding stent 206 which has a plurality of struts 208 and bends 210. The self expanding stent 206 is shown in FIG. 12.

The self expanding stent 206 has a valve member 212 formed from a piece of biocompatible graft material stitched onto spaced apart struts 208 to provide a part cylindrical surface on the self expanding stent 206 to form a valve assembly 214.

Around the lower circumference of the valve member 212 is a portion of resilient wire 213 retained by stitching 215 to assist with retaining the part circular shape of the valve member to endure good sealing against the inside surface of the tubular body of the longer leg 200.

This valve assembly is stitched into the tubular body of the longer leg 200 by stitching 216 at the bends 210 so that the valve member underlies the fenestration 202 and closes off the fenestration to flow therethrough from inside the longer leg to outside. A cross section of the valve at this stage is shown in FIG. 13.

Substantially opposite to the fenestration 202 in the tubular longer leg 200 a side arm 218 extends from a fenestration 220 in the tubular longer leg 200. The side arm 218 is in this embodiment formed from a corrugated graft material.

Figure 13:
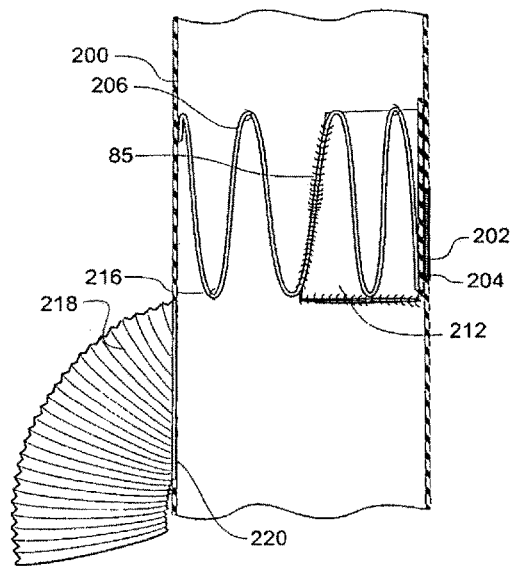
FIG. 13 shown a cross-section thought valve arrangement of FIG. 11.
Figure 14:
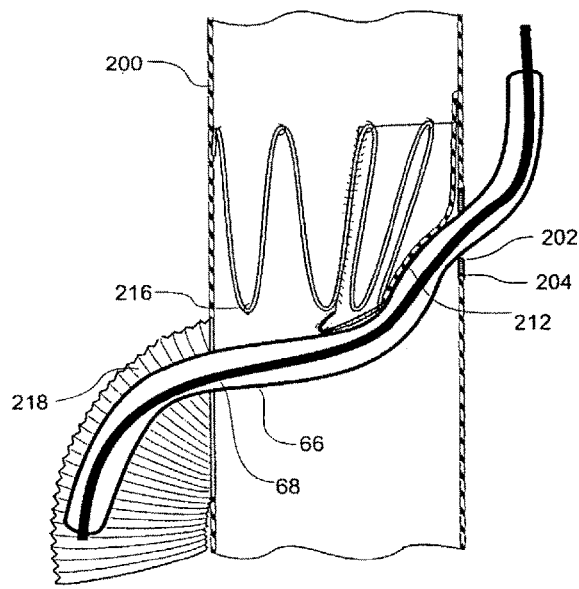
FIG. 14 shows the valve arrangement of FIGS. 11 and 13 with an indwelling catheter extending through it.

FIG. 14 shows the embodiment as shown in FIG. 13 except that an indwelling catheter 66 and guide wire 68 through the indwelling catheter extend through the side arm 218 and through the fenestration 202 and this lifts the valve member 212 off the fenestration 202 against the restoring force of the resilient self expanding stent 206.

FIG. 15A to 15M show the various stages of deployment of a stent graft according to one embodiment of the present invention.

Figure 15A:
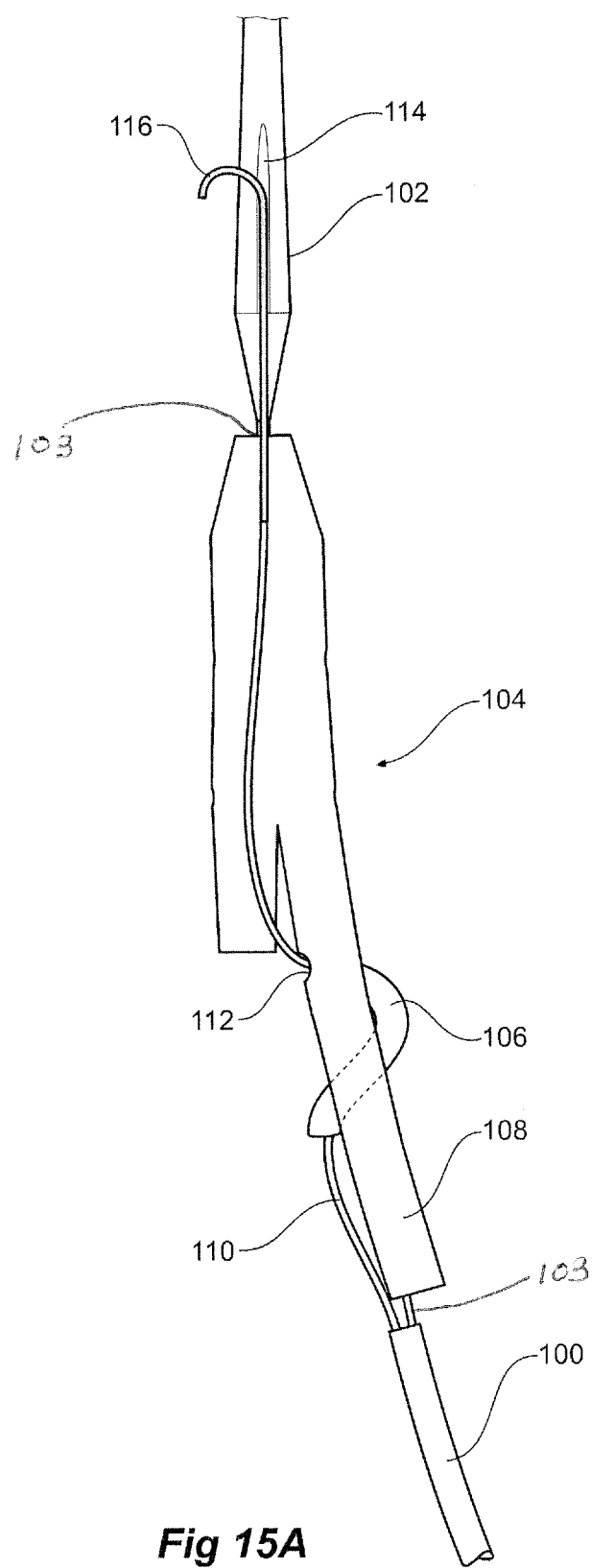
FIG. 15A to 15M show the various stages of deployment of a stent graft according to one embodiment of the present invention.

FIG. 15A shows a schematic version of one embodiment of a stent graft according to the present invention loaded onto a delivery device. For convenience the sheath of the delivery device has been withdrawn to show the assembly inside it. The delivery device 100 has an inner cannula that is a guidewire catheter 103 extending through the delivery device and the stent graft 104. A nose cone dilator 102 is attached to the inner cannula 103 at the proximal end of the delivery device 100. A stent graft assembly 104 according to one embodiment of the present invention is mounted over a portion of the inner cannula 103. This embodiment of stent graft 104 has a helical side arm 106 on the longer leg 108 of the stent graft 104. An indwelling catheter 110 extends from the deployment device 100 through the helical side arm 106 exiting at valved aperture 112 and extending to a groove 114 in the nose cone dilator 102 outside of the stent graft 104. The indwelling catheter 110 has a flexible curved proximal end 116. The inner cannula 103 is also shown in FIG. 16A.

Figures 16A, 16B:
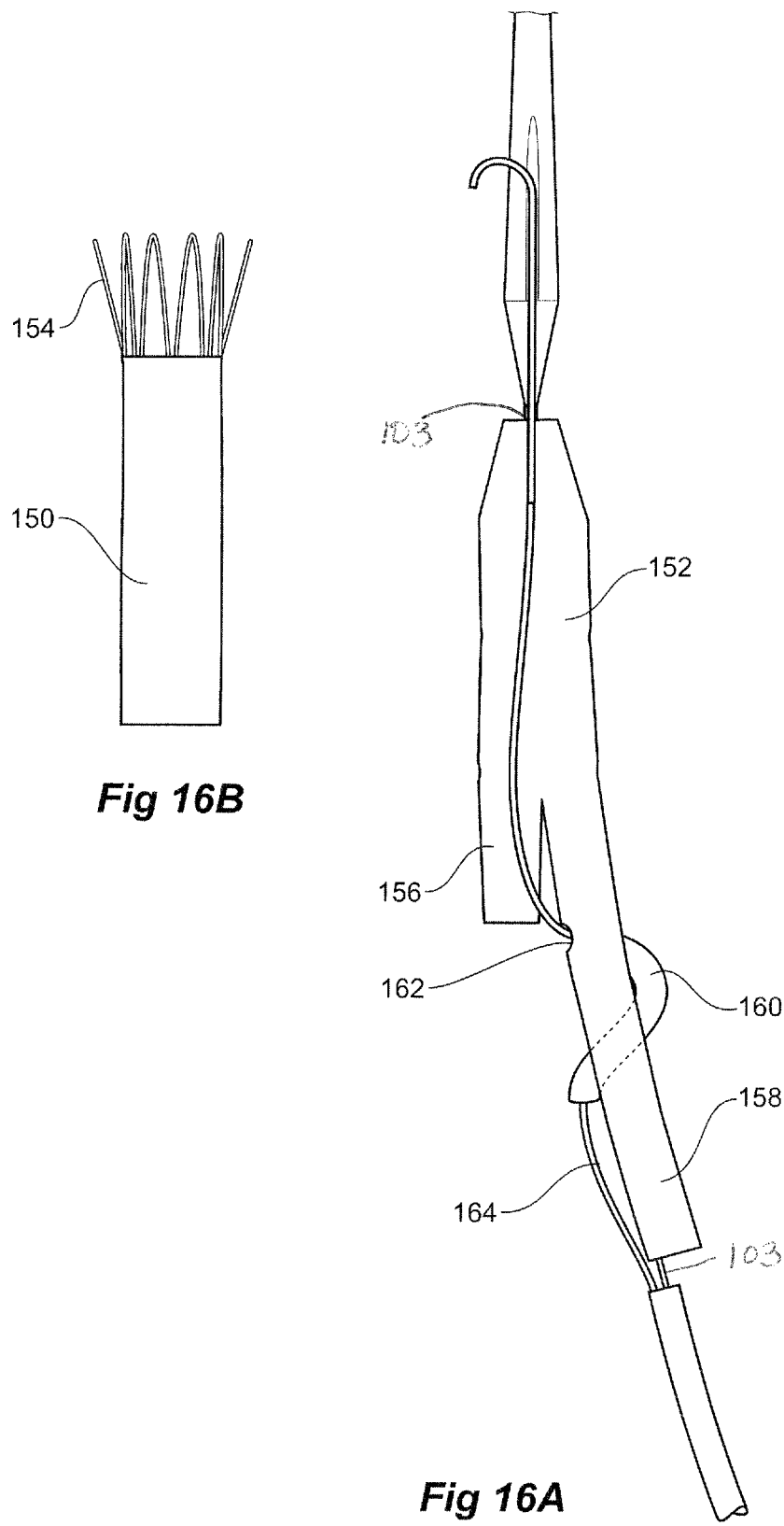
FIG. 16A to 16K show the various stages of deployment of a stent graft according to another embodiment of the present invention.

As the inner cannula or guidewire catheter is shown in at least FIGS. 15A and 16A, no new matter is added. This feature is also shown and described in U.S. Publication No. 2005/0182476 which was properly incorporated by reference in the parent to this case.

Figure 15B:
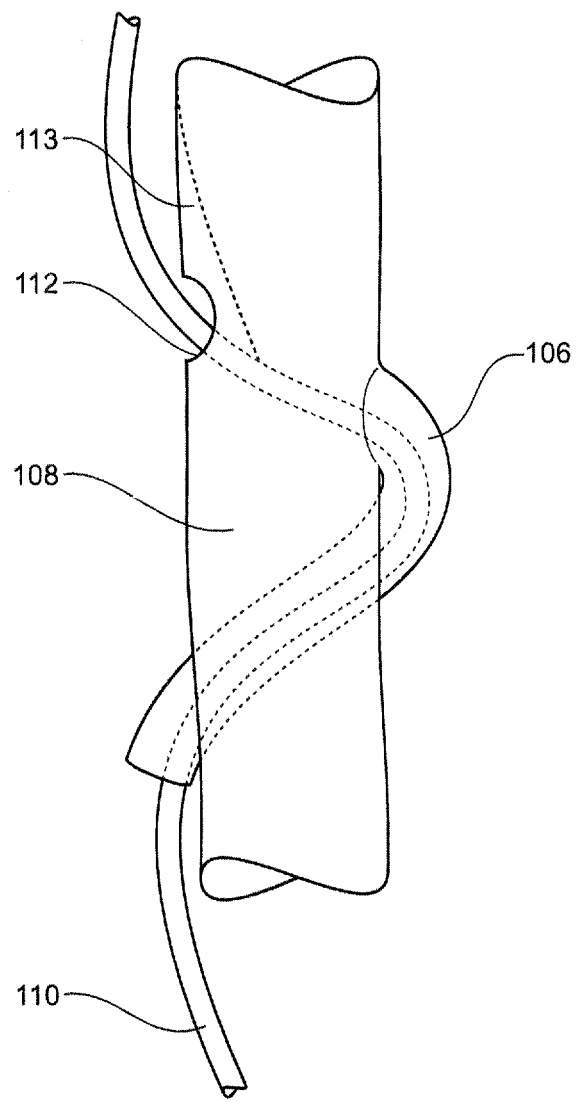

Detail of the tubular side arm 106 and valve arrangement 112 are shown in FIG. 15B. The tubular side arm 106 extends around the longer leg 108 from a fenestration 107 and the indwelling catheter 110 extends into the tubular side arm and out through the valved aperture 112. The valved aperture 112 has a flap valve 113 on its inside to ensure that the aperture is closed when the indwelling catheter is removed. The flap valve is substantially the same as the as the construction shown in FIGS. 3 to 6.

Figure 15C:
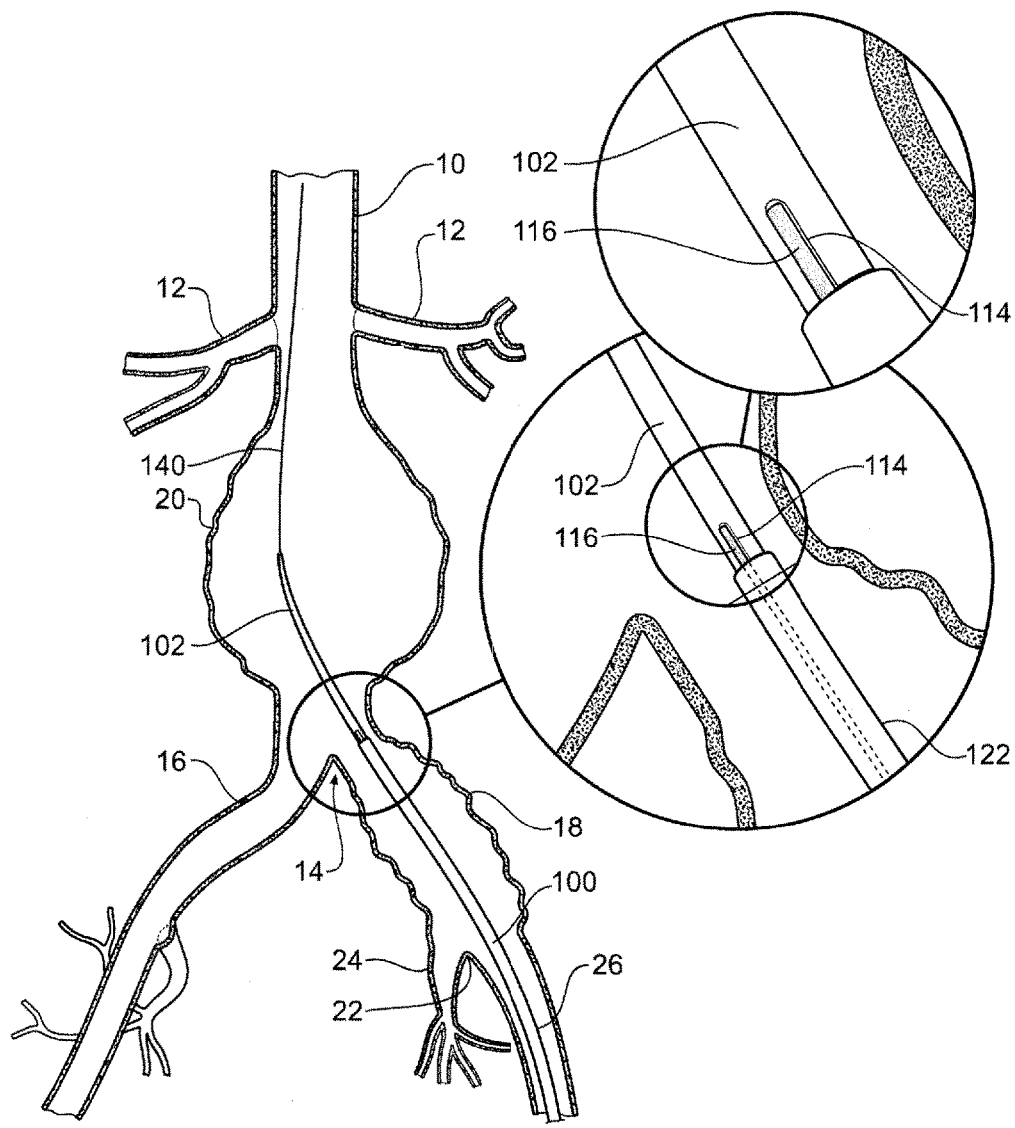

FIG. 15C shows a schematic vasculature of a patient including an aorta 10 renal arteries 12 and an aortic bifurcation 14. Extending from the aortic bifurcation are iliac arteries 16 and 18. The aorta has an aneurysm 20 which extends down the iliac artery to the position of the internal iliac artery 24. The iliac bifurcation 22 defines the bifurcation between the internatal iliac artery 24 and the external iliac artery 26.

As shown in FIG. 15C the deployment device 100 has been deployed over a guide wire 120 so that its nose cone 102 extends up into the aneurysm 20 and the distal end of the nose cone 102 is substantially adjacent to the aortic bifurcation 14. As shown in the detail in FIG. 15C the indwelling catheter and particularly its curved tip 116 has been compressed by the sheath 122 into the groove 114 in the nose cone dilator.

Figure 15D:
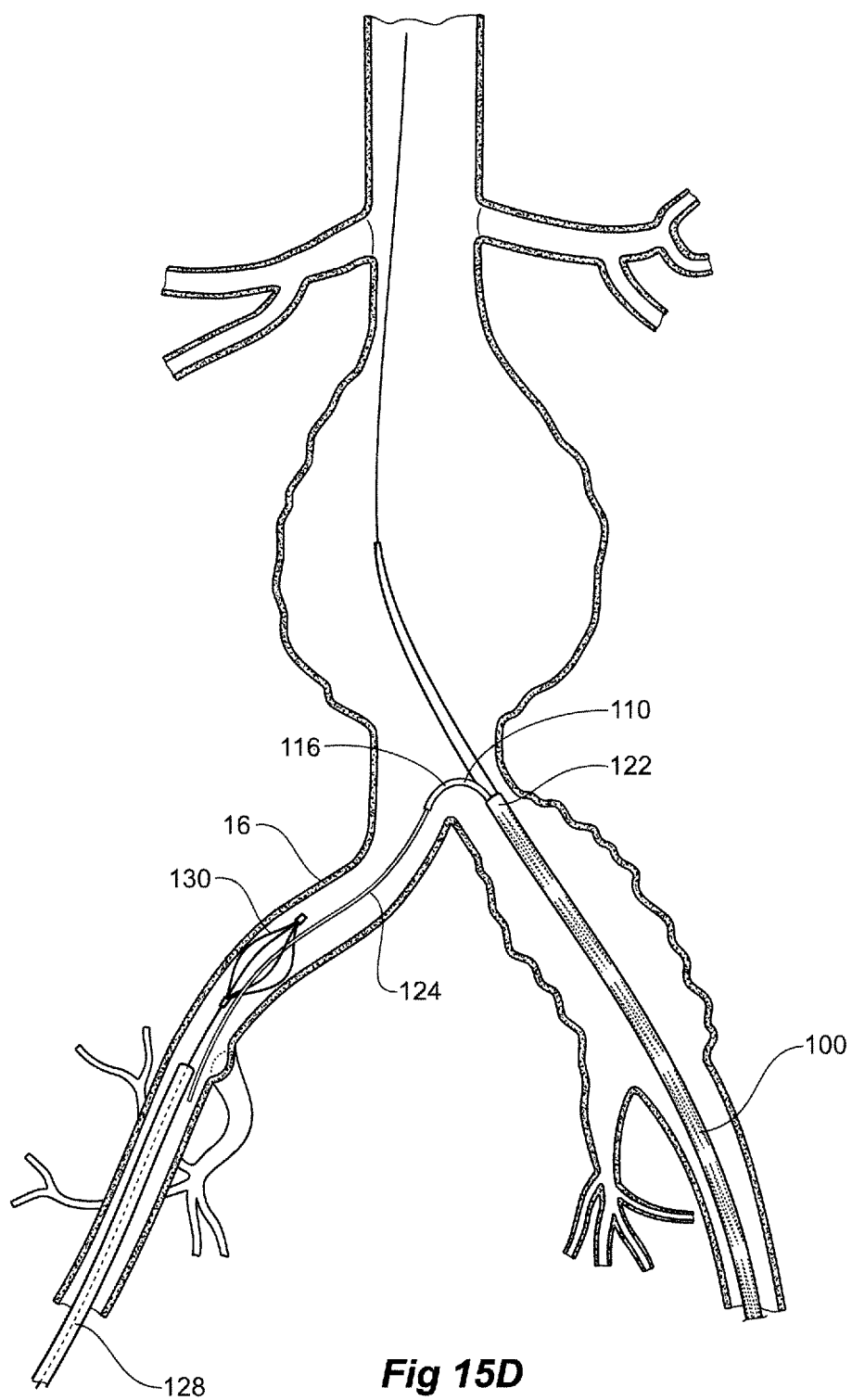
Figure 15E:
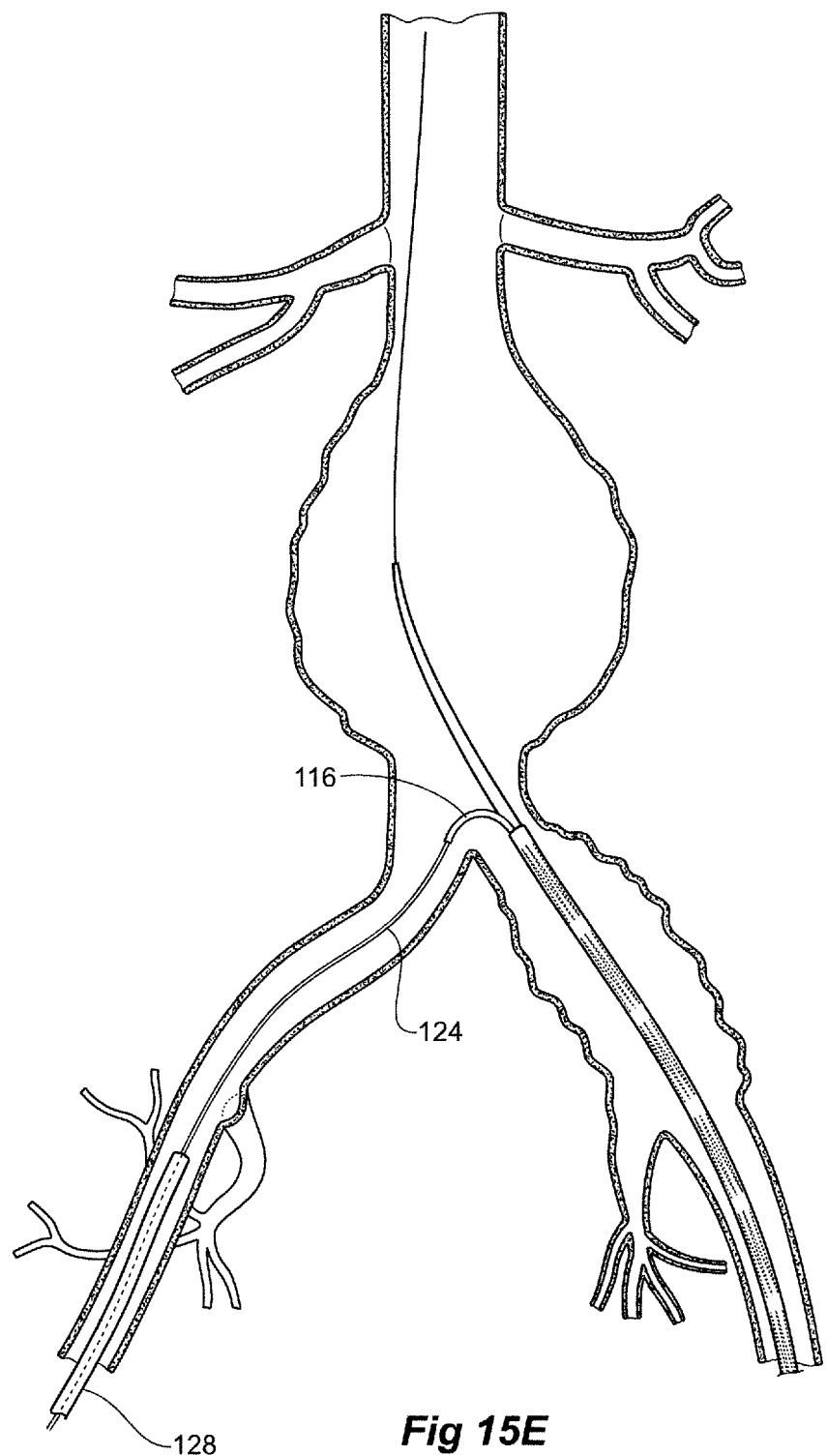

As shown in FIG. 15D the sheath 122 of the deployment device has been withdrawn slightly to release the curved tip 116 of the indwelling catheter 110 and the indwelling guide wire 124 from the indwelling catheter 110 has been extended. Because of the curved end of the indwelling catheter the indwelling guide wire 124 has extended down the contra-lateral iliac artery 16. A snare catheter 128 has been deployed into the contra-lateral common iliac artery and a snare 130 of the snare catheter 128 has been extended to grasp the guide wire 124. The guide wire 124 is extracted via the snare catheter 128 so that it becomes a through-and-through guide wire. It is important at this stage to ensure there is slack maintained in the guide wire at the aortic bifurcation to prevent damage to the aortic bifurcation. This position is shown in FIG. 15E.

The use of and indwelling catheter with a curved tip to facilitate snaring from a contralateral iliac artery is taught in U.S. patent application Ser. No. 11/600,655 entitled 'Stent Graft Introducer' and the teaching therein is incorporated herein in its entirety.

Figure 15F:
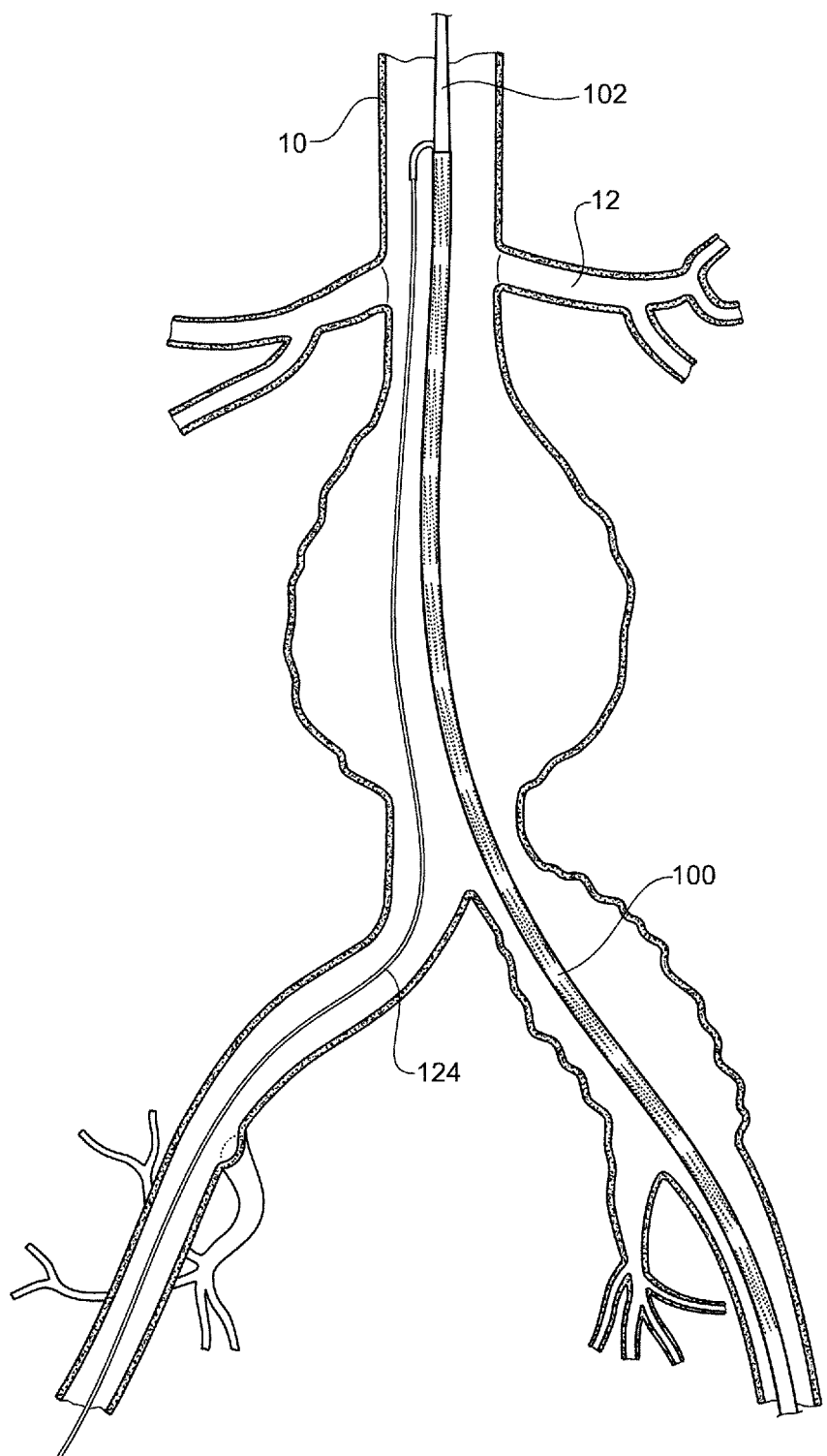

As shown in FIG. 15F the deployment device 100 in then advanced so that the nose cone dilator 102 is proximal of the renal arteries 12. This draws the indwelling guide wire 124 also up into the aorta 10.

Figure 15G:
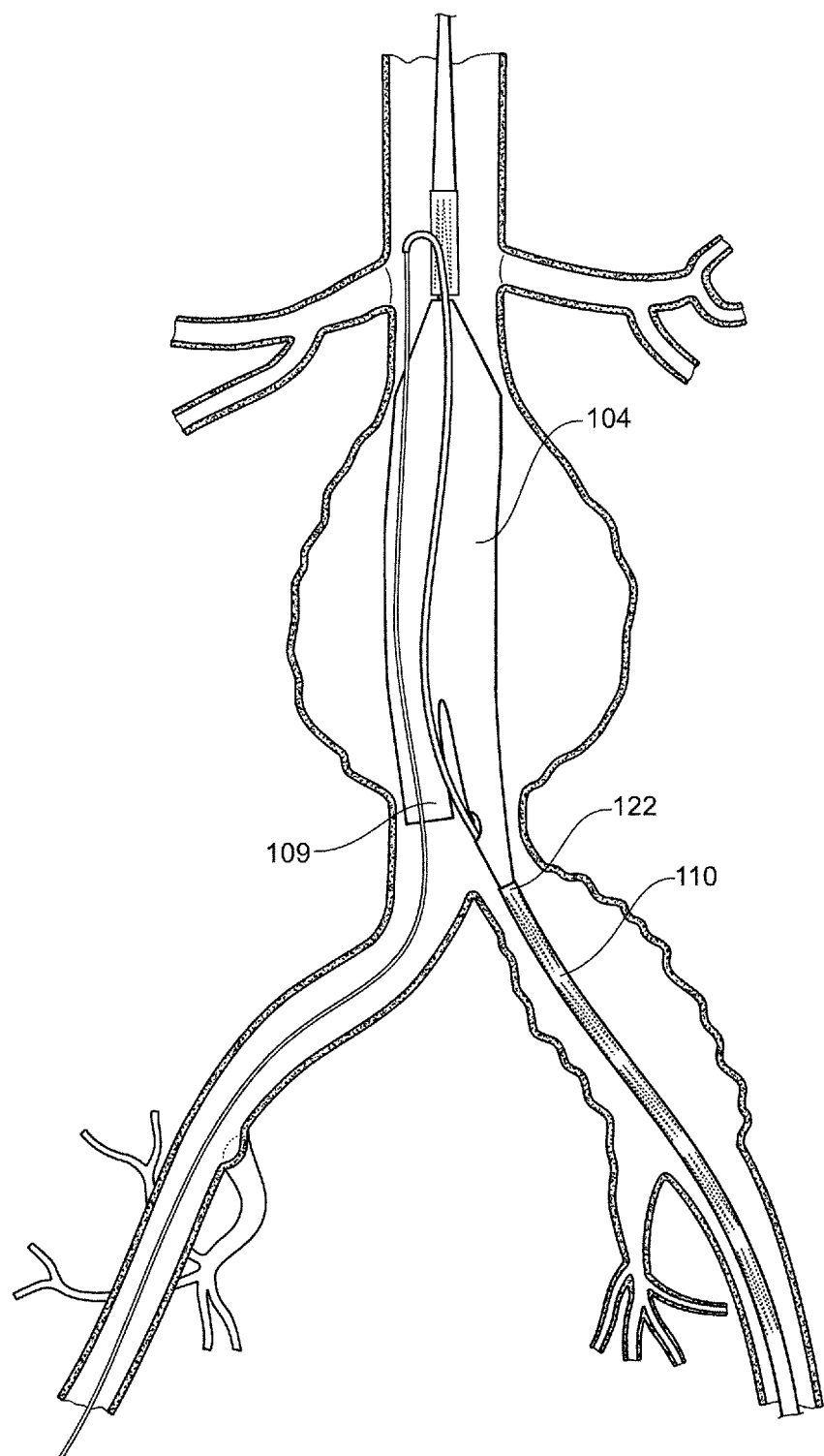

The sheath 122 of the deployment device 110 is then withdrawn to release the shorter leg 109 of the stent graft 104. This stage is shown in FIG. 15G.

Figure 15H:
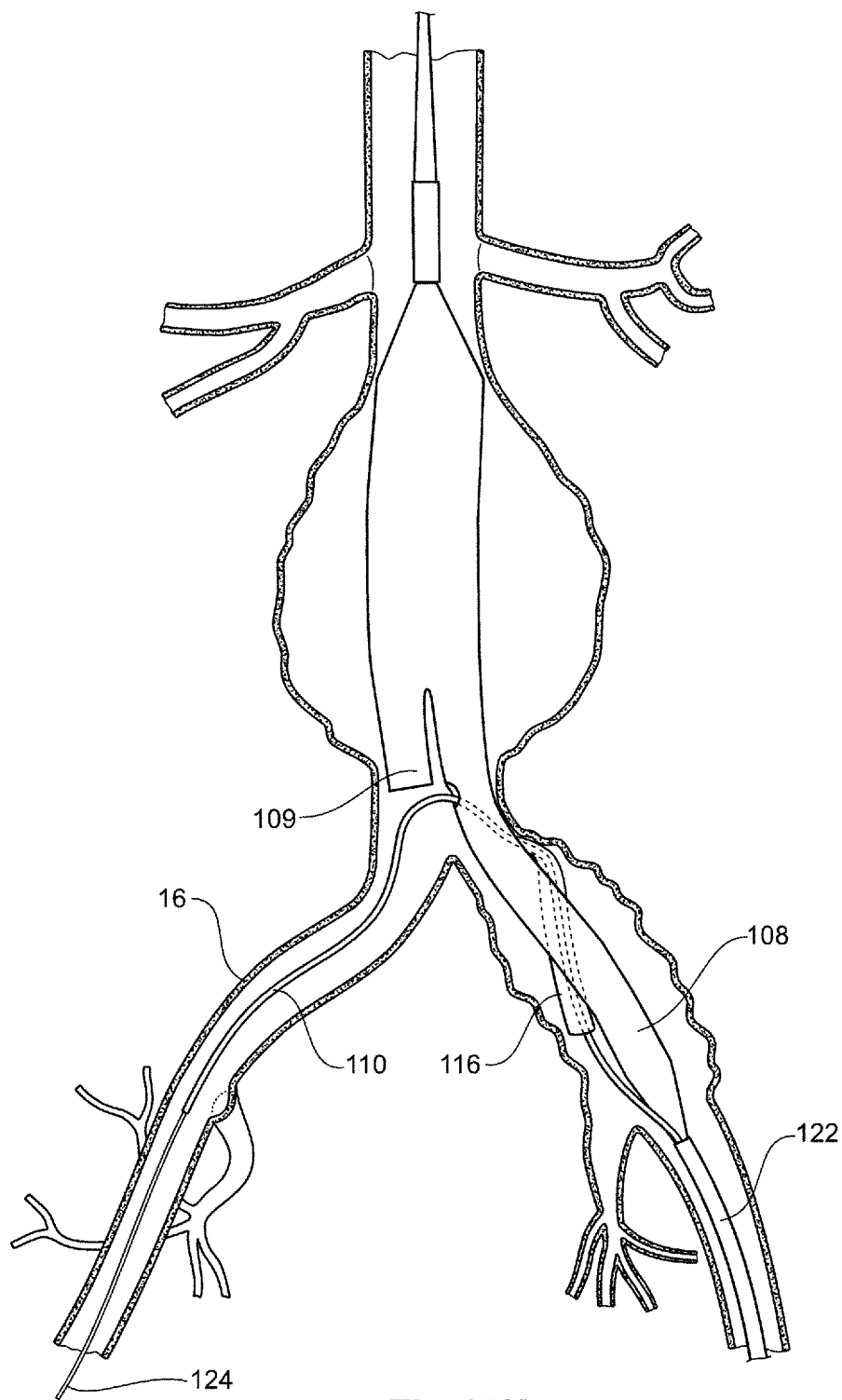

As shown in FIG. 15H the indwelling catheter is withdrawn down into the contra-lateral iliac artery 16 and the sheath 122 is withdrawn so that it is distal of the distal end of the side arm 106 while still retaining the distal end of the longer leg 108.

Figure 15I:
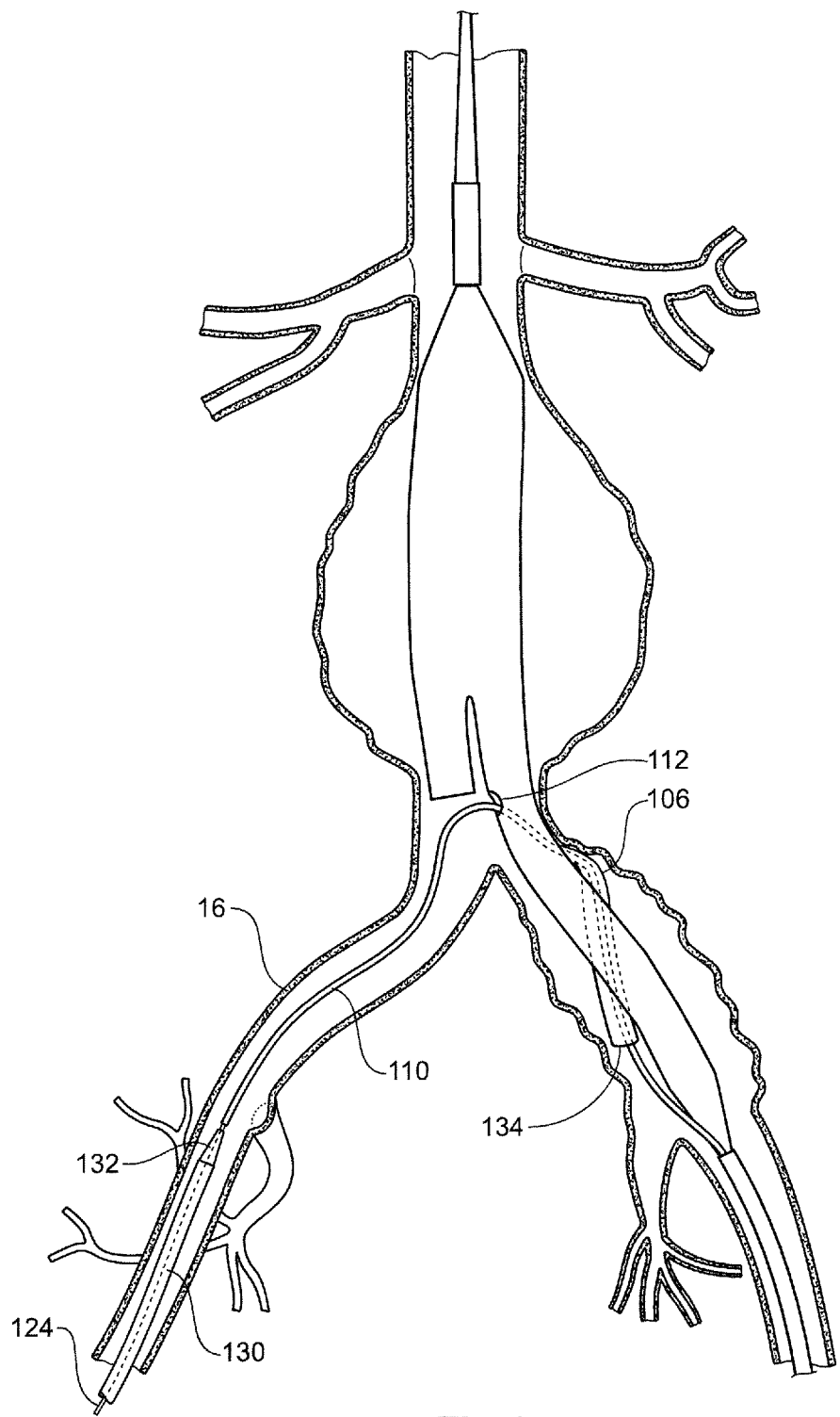
Figure 15J:
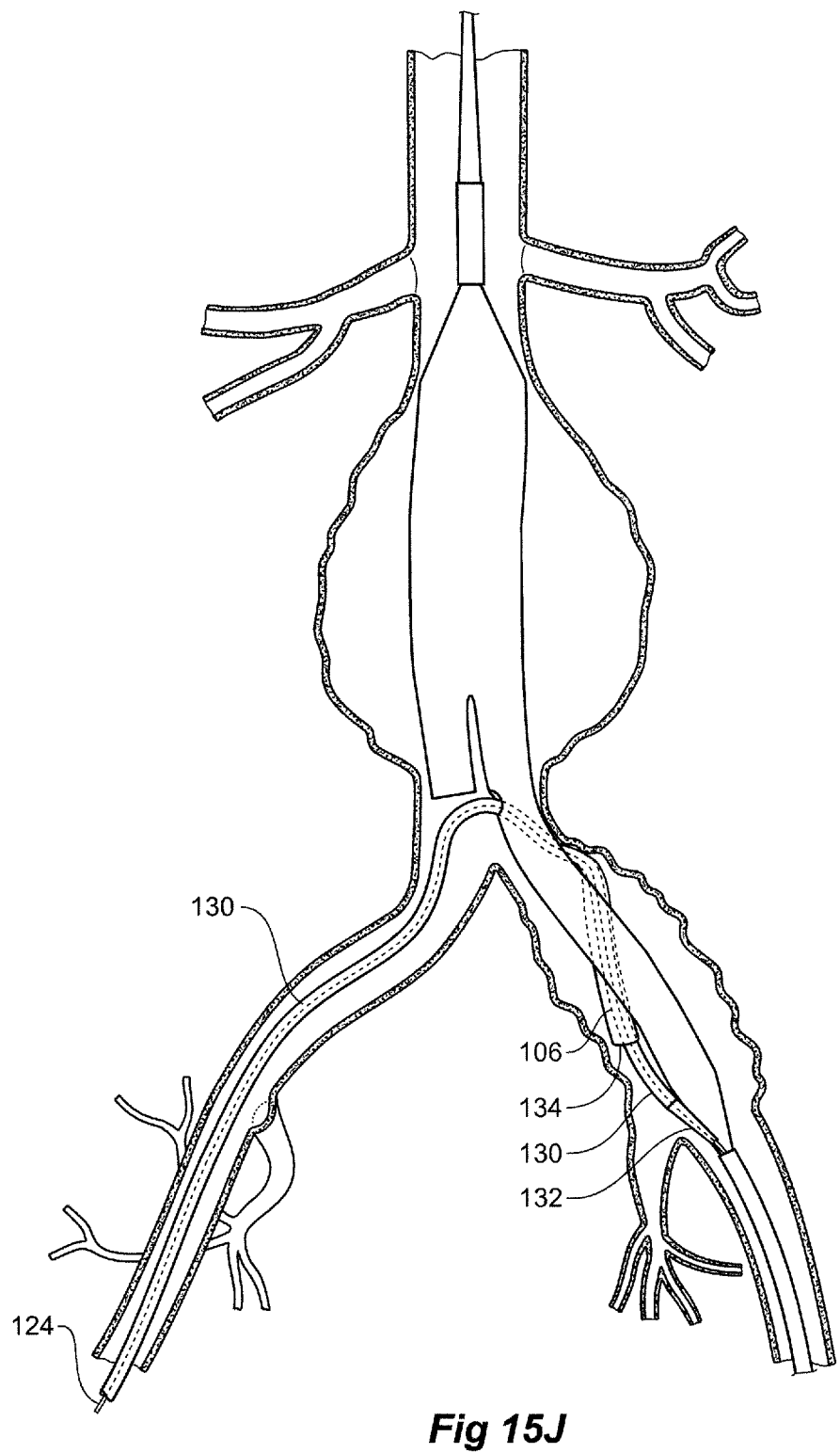
Figure 15K:
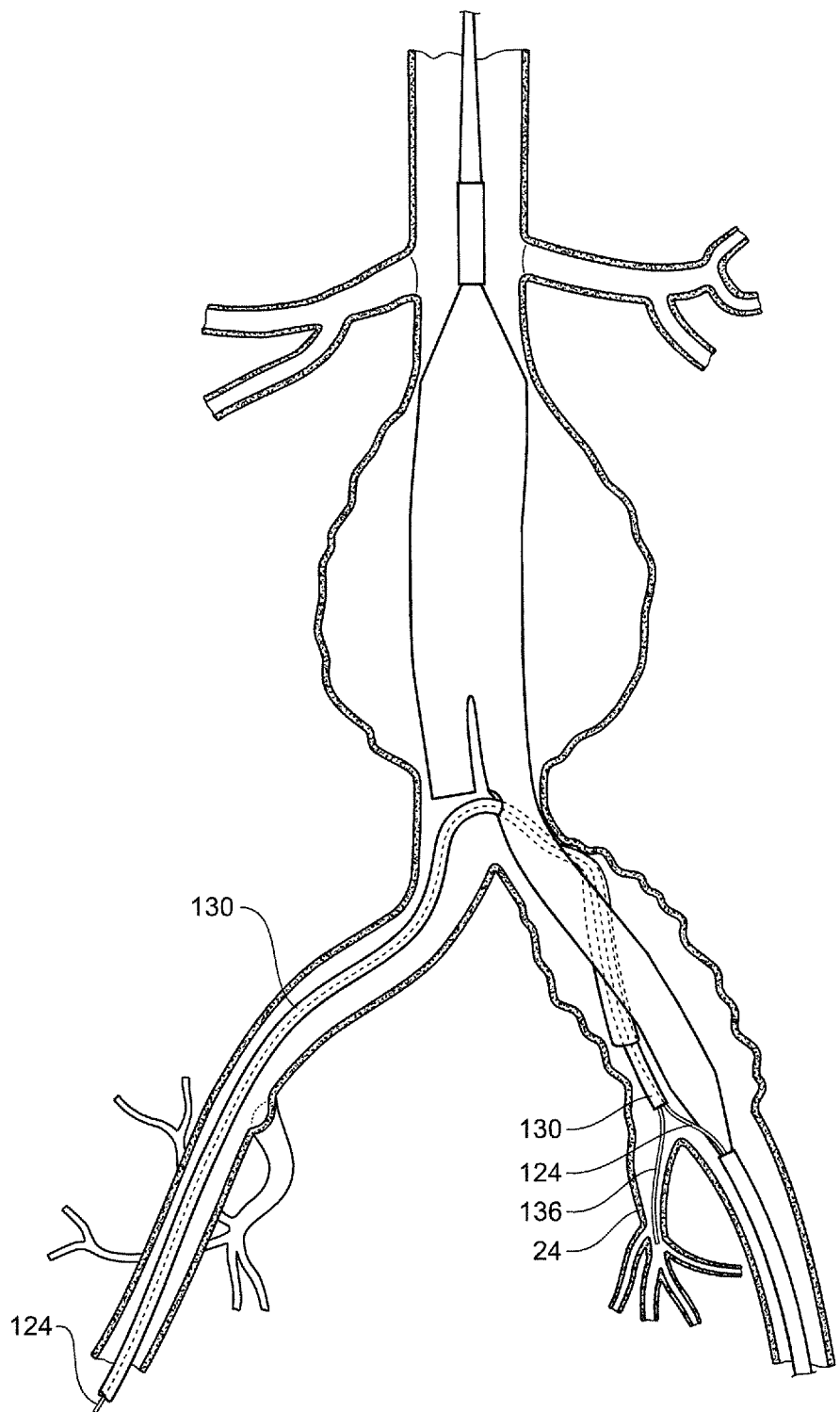

As shown in FIG. 15I a dilator and sheath introducer 130 is advanced over the guide wire 124 in the contra-lateral iliac artery 16 and the indwelling catheter 110 and extension arm deployment device are tracked over the guide wire 124 so that the nose cone 132 of the sheath introducer enters the valved aperture 112 and tracks over the guide wire 124 into the side arm 106 until it exits the distal end of the side arm 134 as shown in FIG. 15J. The sheath introducer nose cone 132 is then withdrawn leaving the sheath 130 in place. At this stage the indwelling guide wire 124 is still in a through-and-through position. As shown in FIG. 15K, another guide wire 136 is introduced through the sheath 130 and extended from the sheath 130 to enter into the internal iliac artery 24.

Figure 15L:
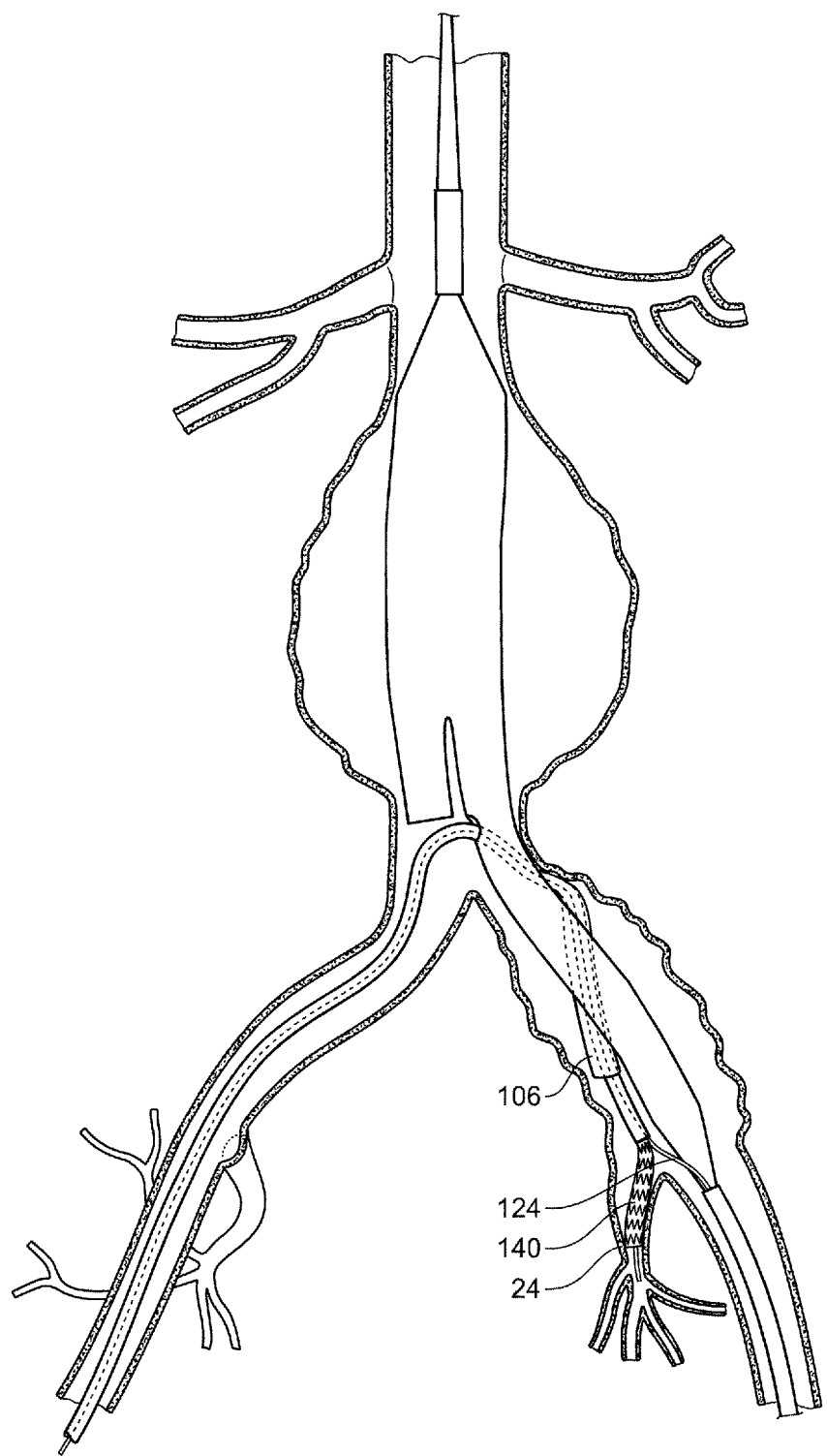
Figure 15M:
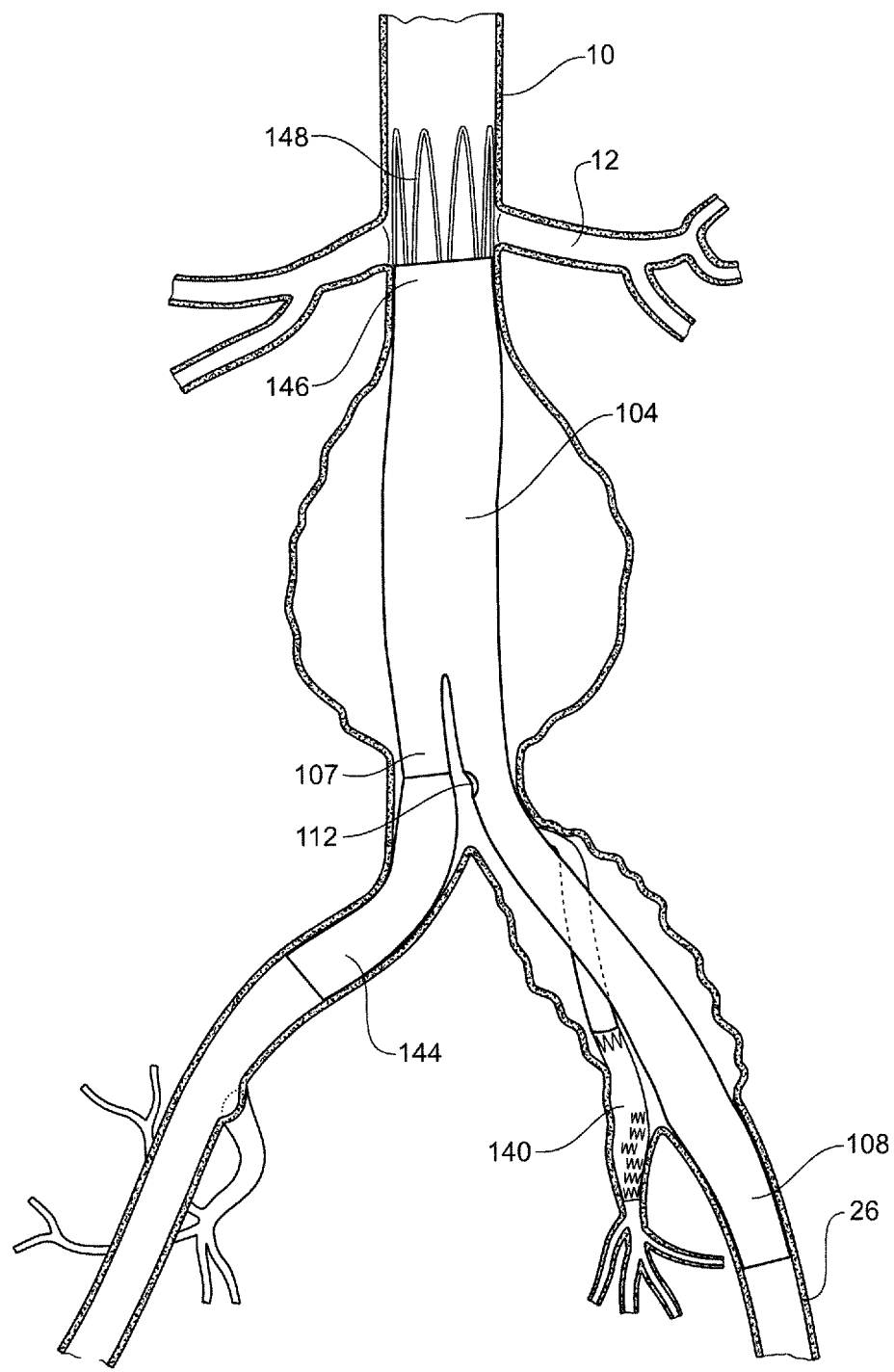

As shown in FIG. 15L a side arm deployment device is deployed over the guide wire 136 into the internal iliac artery 24 so that balloon expandable covered stent 140 extends into the internal iliac artery 24 from the side arm 106. As shown in FIG. 15M, the indwelling guide wire 124 is then removed and the position of the distal end of the longer leg 108 is set into the external iliac artery 26 and the balloon expandable covered stent 140 is expanded. The sheath 130 is then withdrawn and the valve 112 automatically closes. A leg extension 144 is then placed into the short leg 107 of the graft 104. The proximal end 146 of the stent graft is also released from the deployment device 100 such that a portion of the graft seals into a non-aneurysed portion of the aorta 10 distal of the renal arteries 12 while an uncovered suprarenal stent 148 extends over the renal arteries to provide secure fixation.

FIGS. 16A to 16K show an alternative embodiment of stent graft according to the present invention and the process of deploying such a stent graft in the vasculature of a patient.

The stent graft in this embodiment comprises a two piece body with a proximal portion 150 and a distal portion 152 which when joined together into the vasculature of the patient provide a composite stent graft. The proximal portion 150 has the proximally extending suprarenal stents 154 and the distal portion 152 is bifurcated with a shorter leg 156 and longer leg 158. The longer leg 158 has the helical side arm 160 and the valved aperture 162 through which the indwelling catheter 164 extends.

Figure 16C:
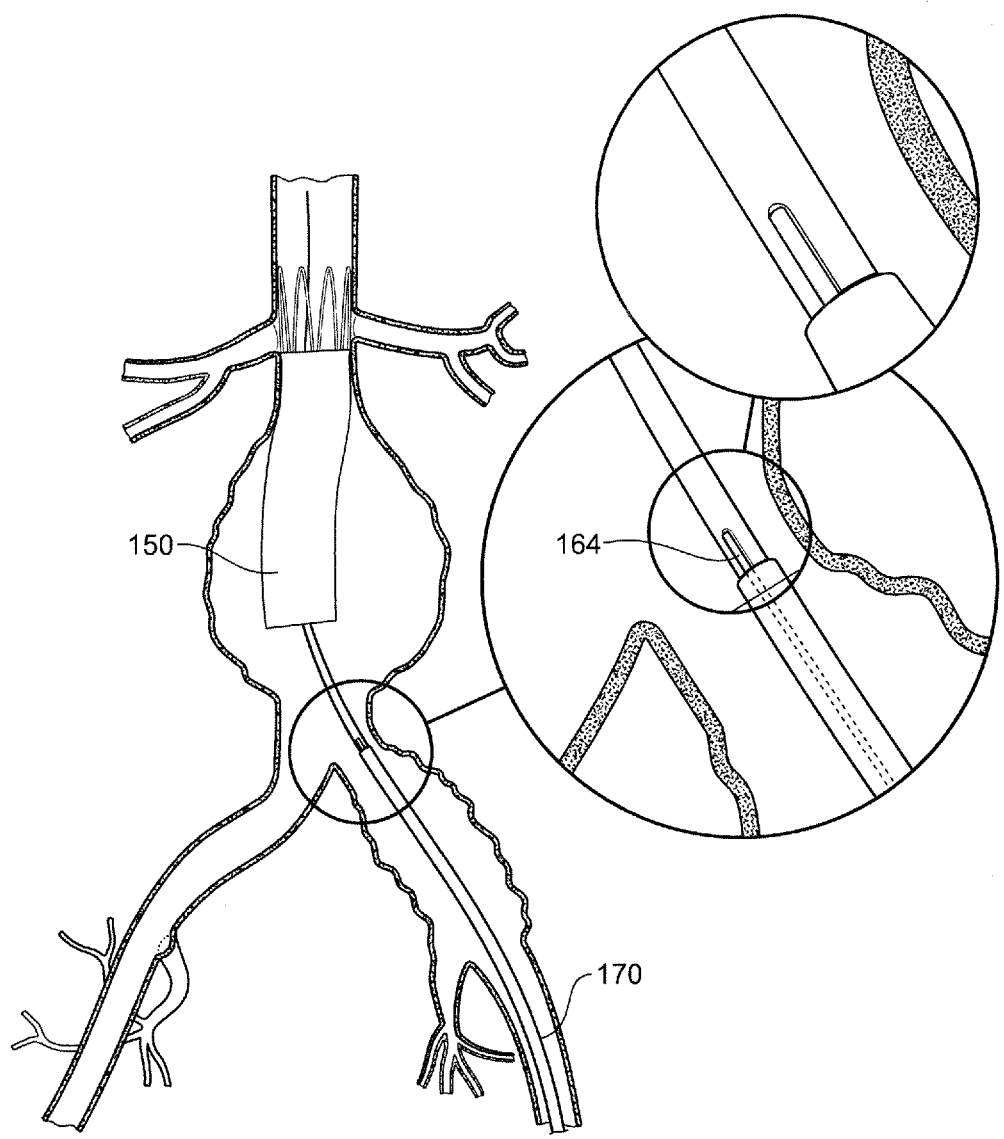
Figure 16D:
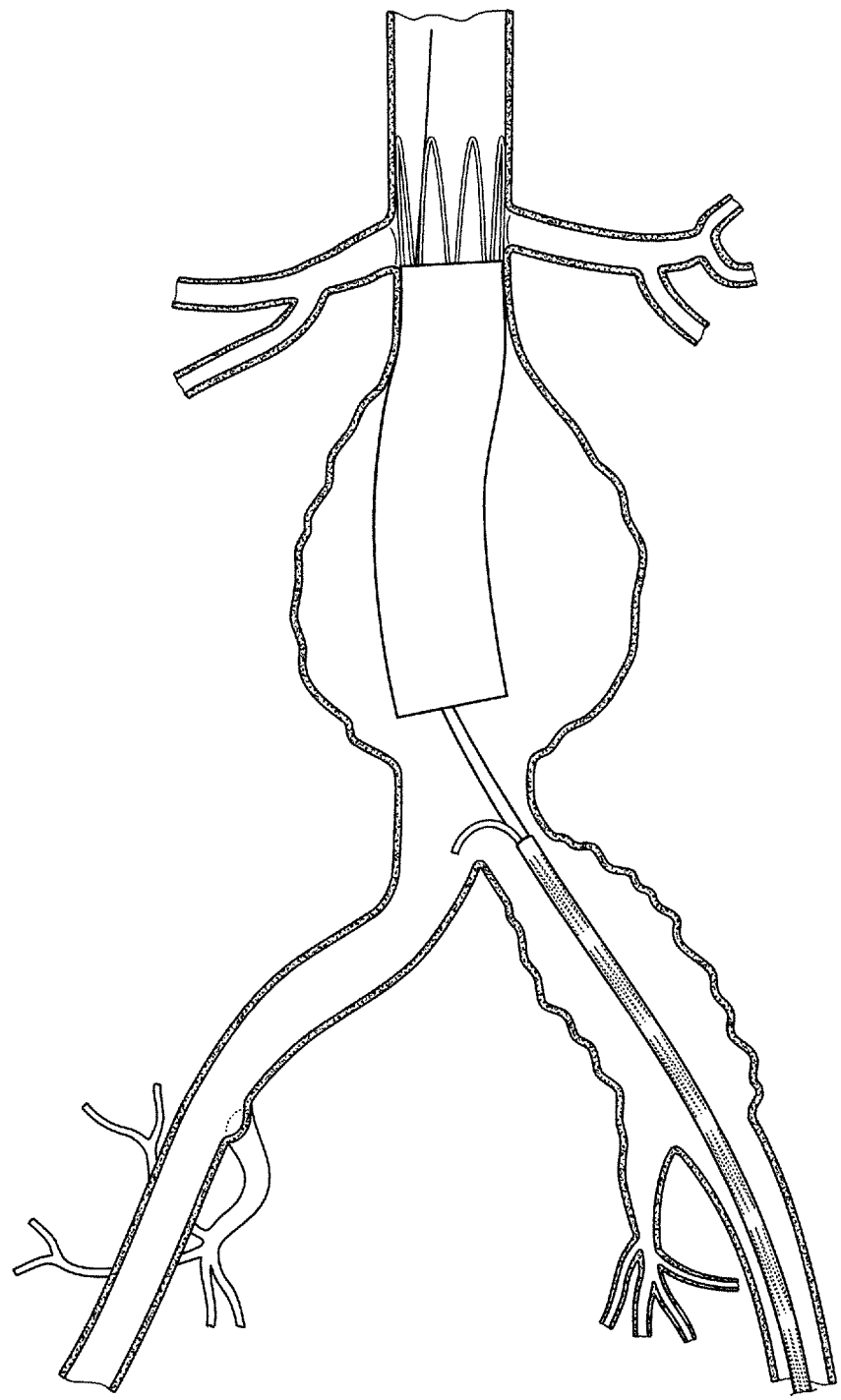
Figure 16E:
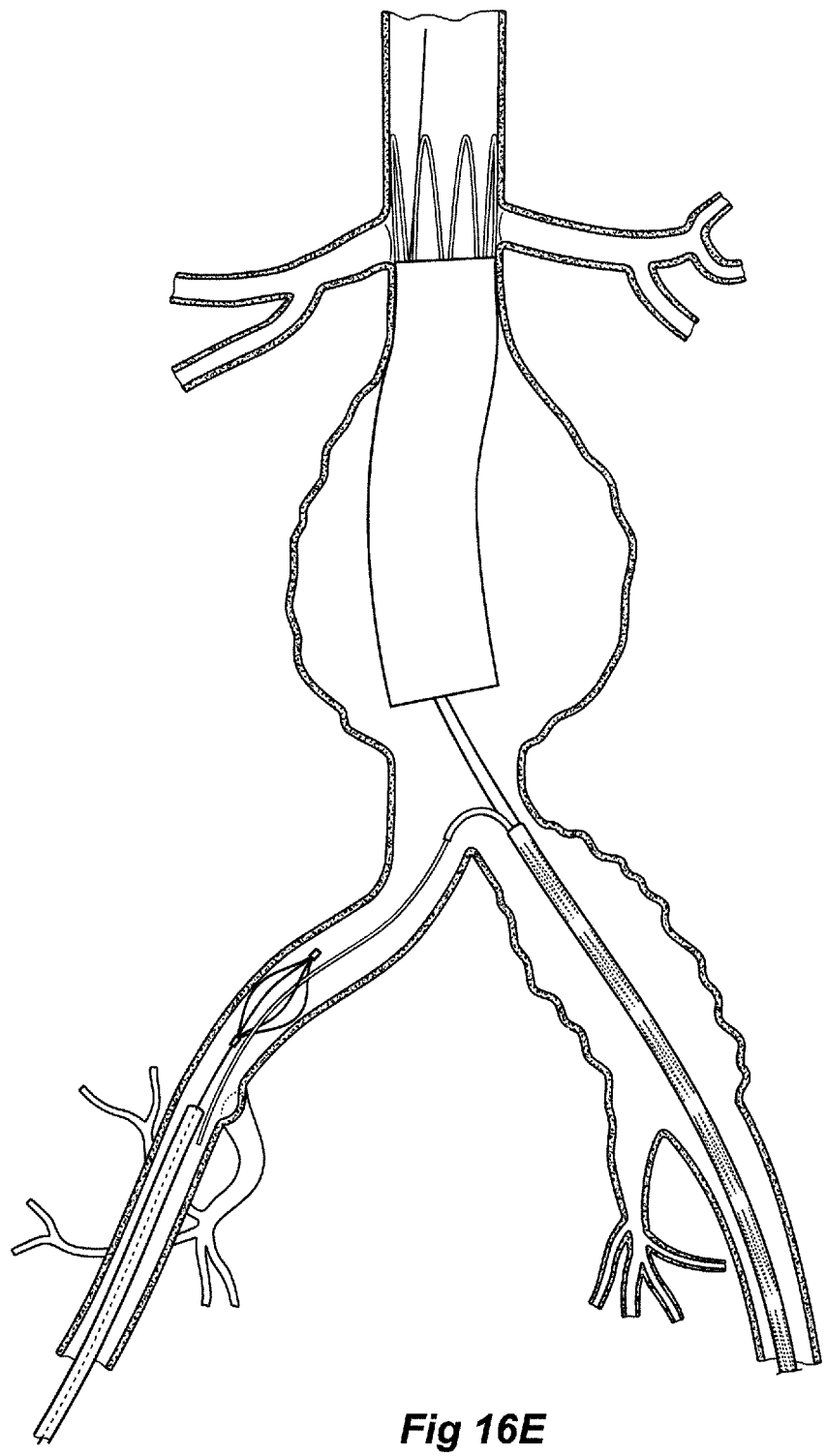
Figure 16F:
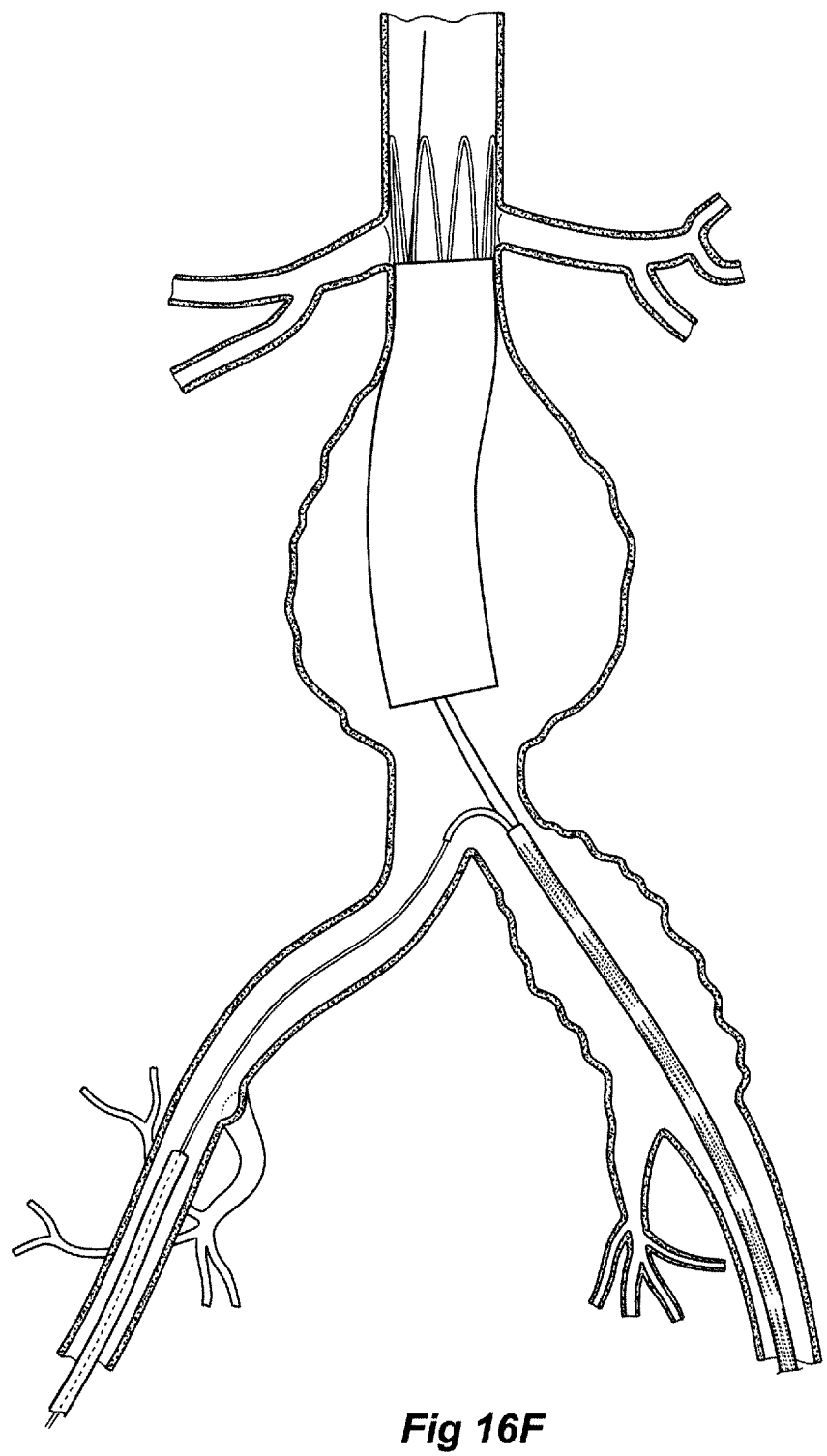
Figure 16G:
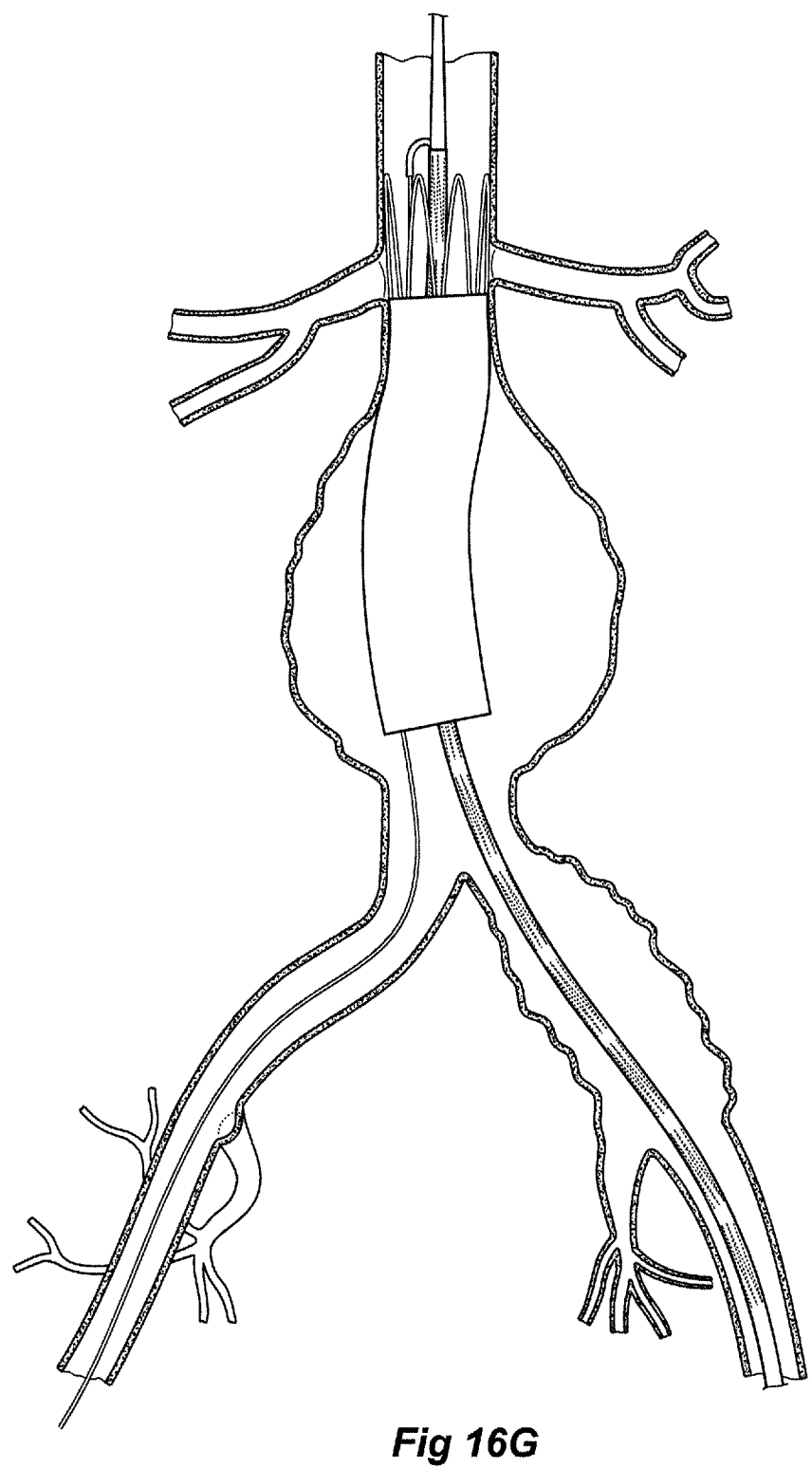
Figure 16H:
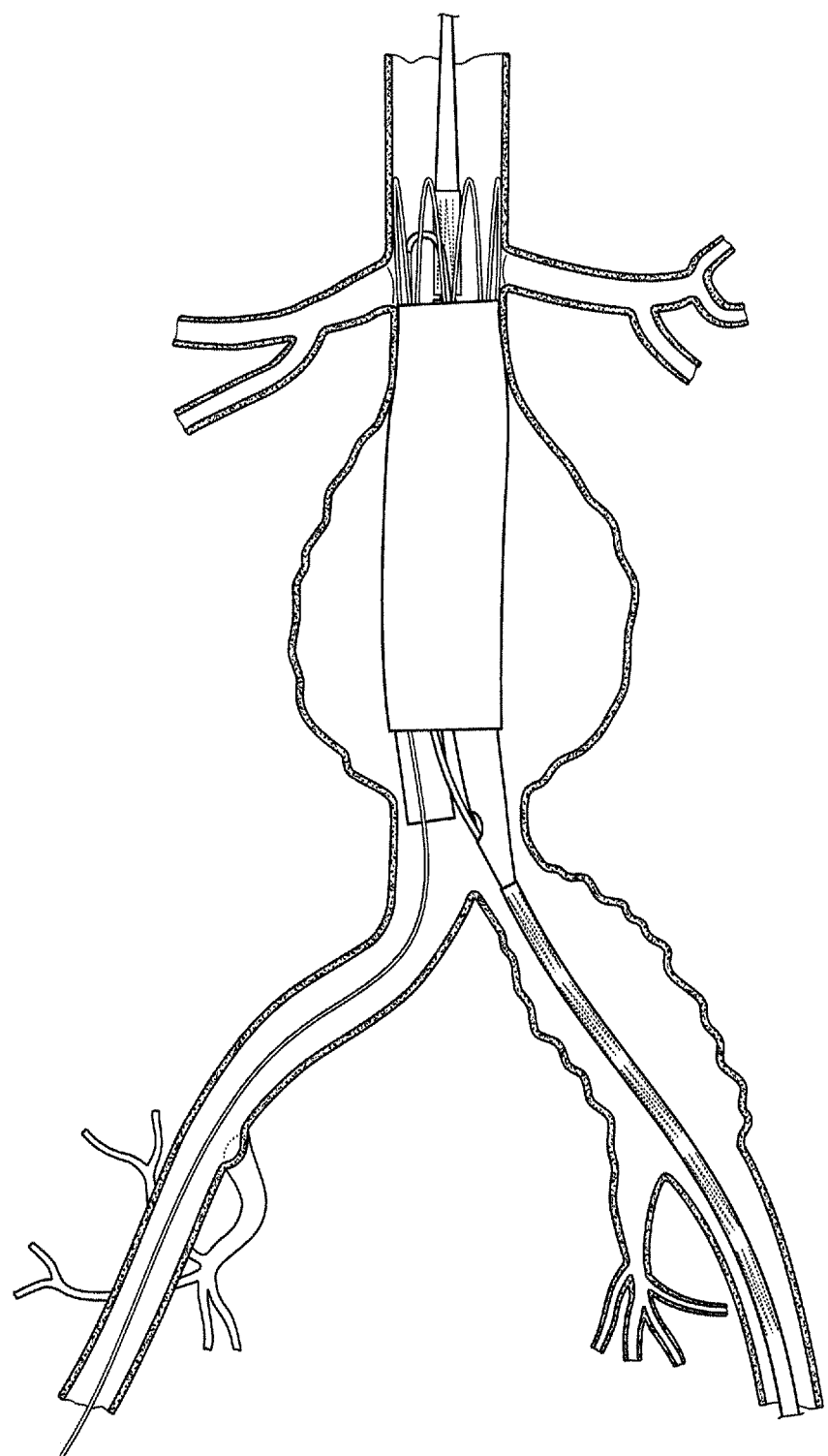
Figure 16I:
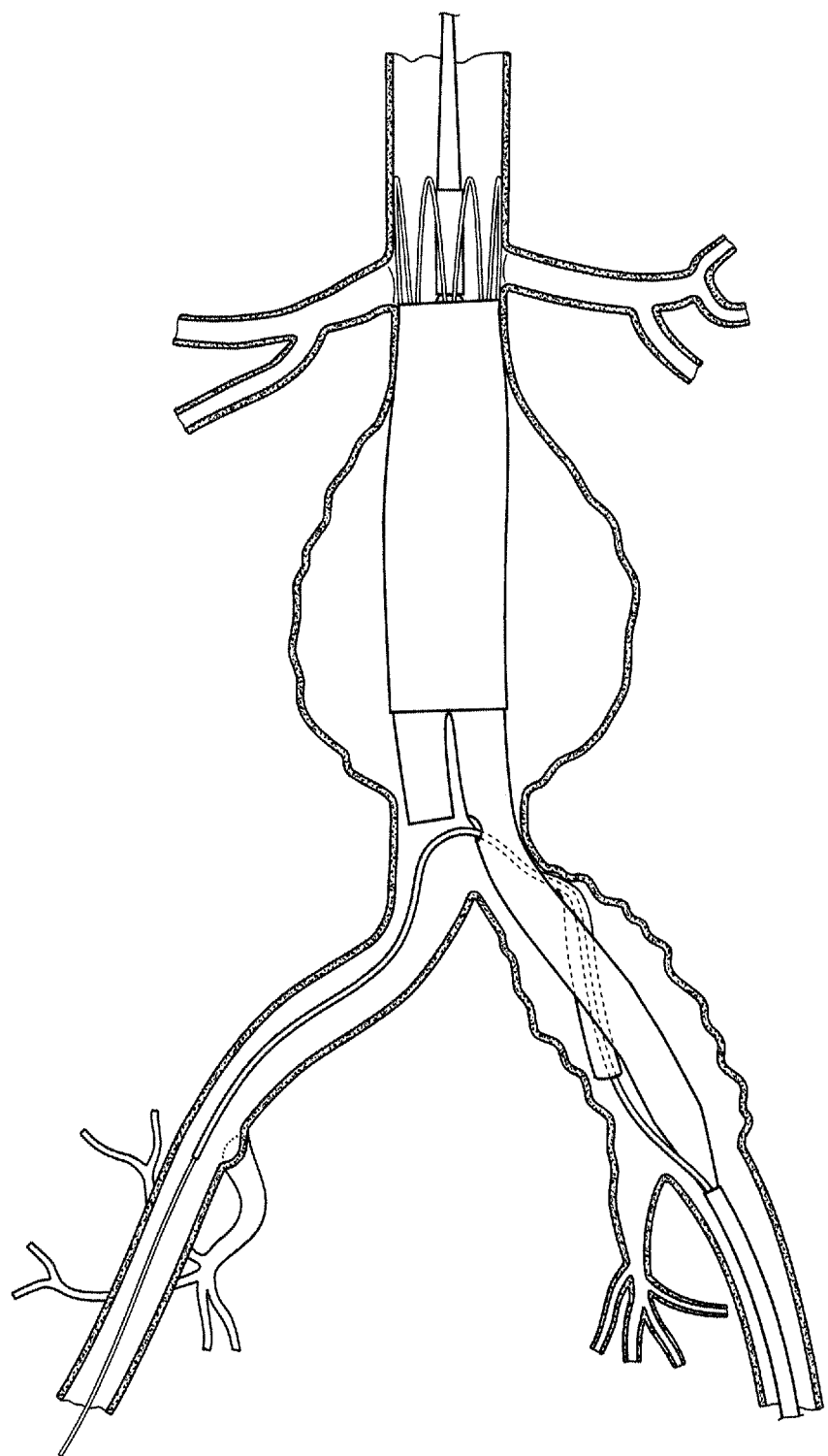
Figure 16J:
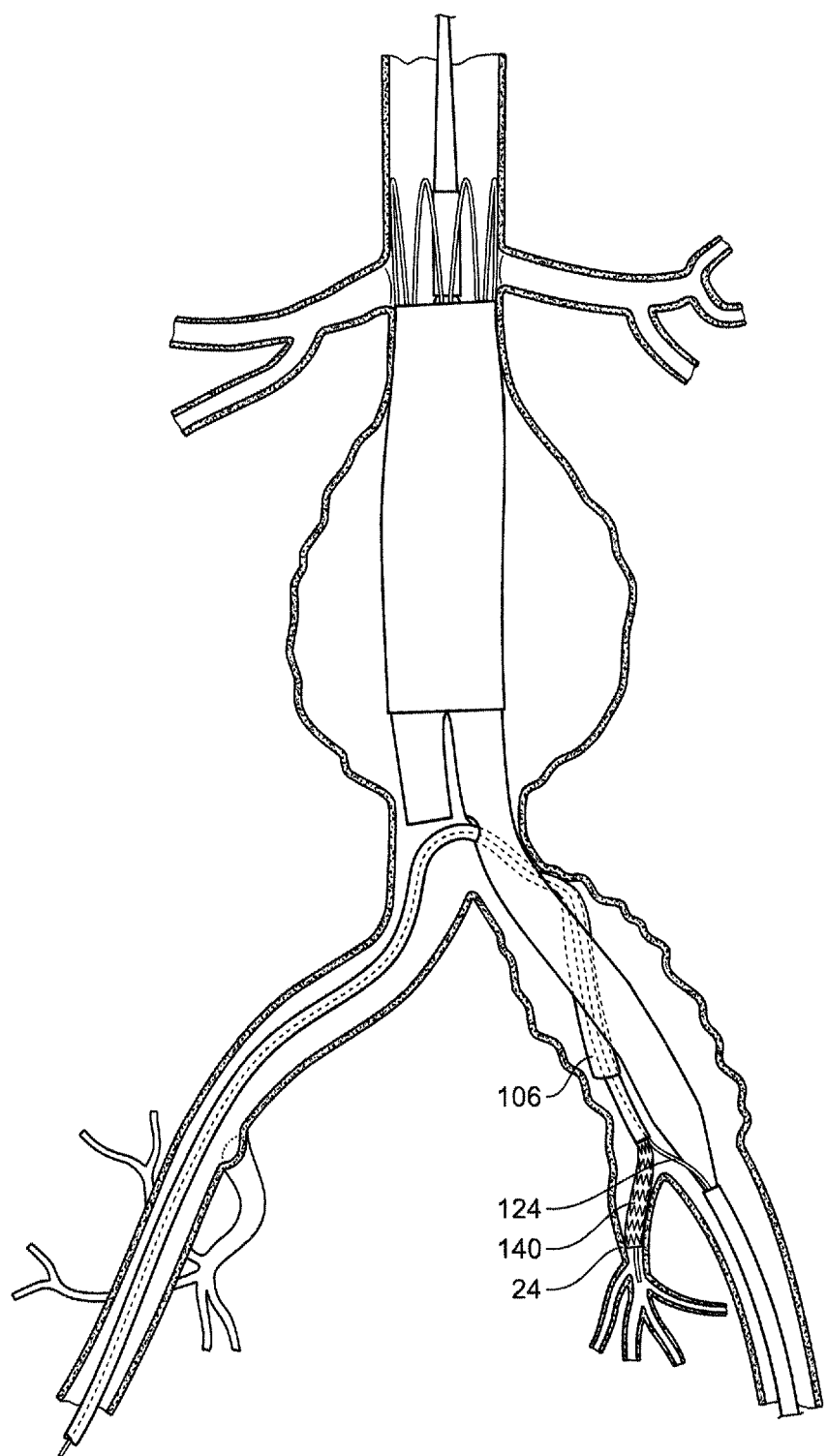
Figure 16K:
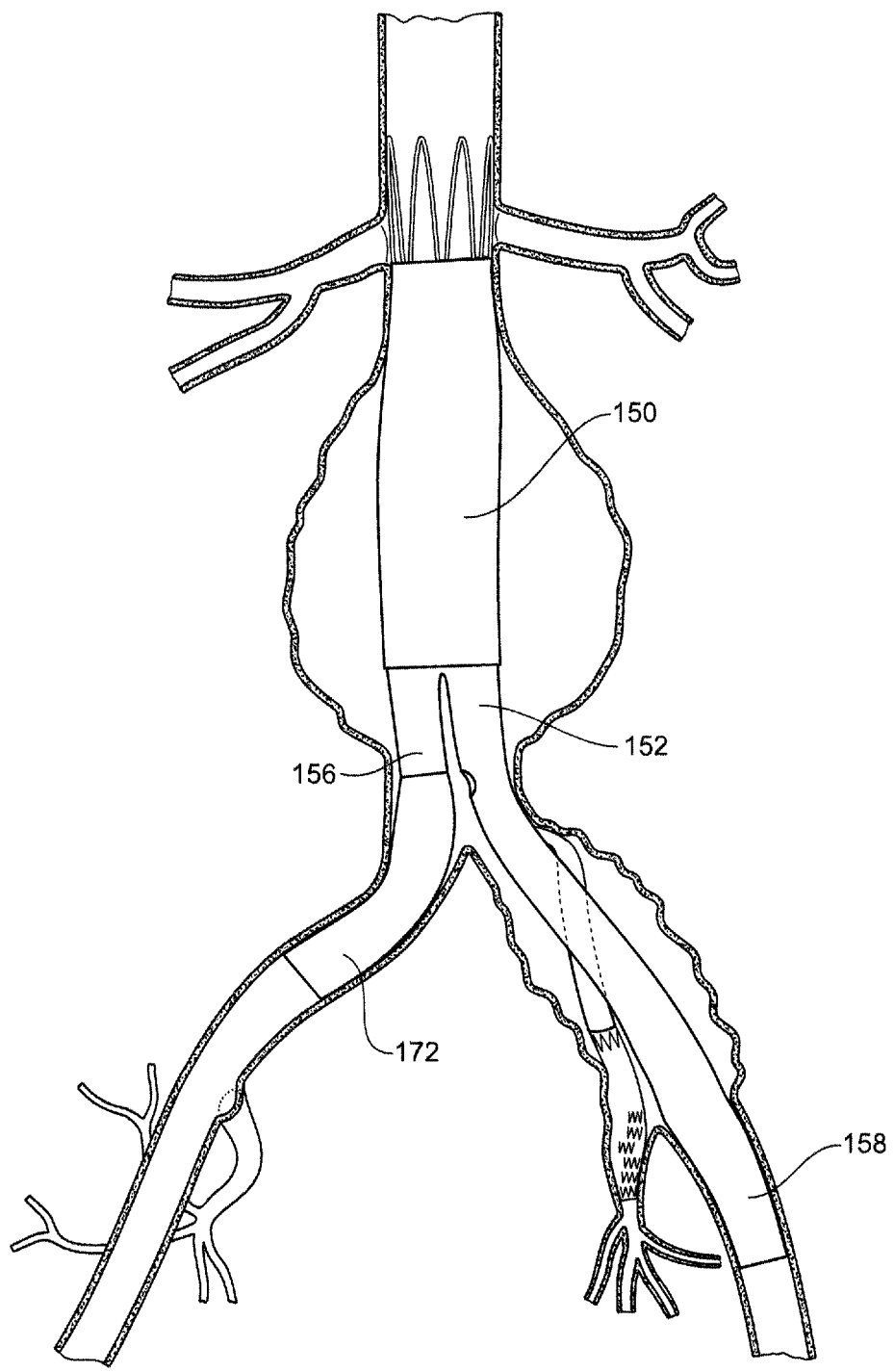

The process of deployment of the stent graft of this embodiment is substantially similar to that shown in FIGS. 15 C to 15M except that, as shown in FIG. 16C, as a first stage the proximal portion 150 is deployed and released into the aorta. Subsequently a separate device 170 with an indwelling catheter 164 is introduced which carries the distal portion 152 and the process of snaring the indwelling guide wire, release of the main stent graft and deployment of a side arm extension into the internal iliac artery as shown in FIGS. 16D to 16J is substantially the same as shown in FIGS. 15C to 15L. The final stage as shown in FIG. 16K of the deployment of the two piece stent graft includes release of the distal portion 152 inside the proximal portion 150 and the deployment of a leg extension 172 into the short leg 156 and release of the distal end of the longer leg 158.

It will be realized that an alternative embodiment access for deployment into the internal iliac artery maybe by a brachial approach and in such case the indwelling catheter in the side arm may extend through the main lumen of the stent graft and the valved aperture may not be necessary in such an embodiment.

Throughout this specification various indications have been given as to the scope of invention but invention not limited to any one of these but may reside in two or more of these combined together. The examples are given for illustration only and not for limitations.

The invention claimed is:

1. A stent graft delivery system for delivering a stent graft to a body vessel of a patient comprising:
   a first delivery device having an inner cannula configured to receive a first guidewire in a lumen of the inner cannula, a nose cone extending from the inner cannula at a delivery end of the delivery device, a stent graft disposed over the inner cannula adjacent to the nose cone, and a retractable sheath disposed over the stent graft;
   wherein the stent graft has a tubular body of a biocompatible graft material having a main lumen, a bifurcation in the tubular body at one end and a first leg and a second leg extending from the bifurcation, the first and second legs having respective first and second lumens and the first and second lumens being in fluid communication with the main lumen;
   wherein the first leg has a sidewall, a first fenestration in the side wall, a side arm attached to the sidewall and extending from the fenestration to define a side arm lumen in fluid communication with the first leg, a valved fenestration in the sidewall circumferentially spaced from the first fenestration, a valve to prevent fluid flow the valved fenestration from inside of the first leg to outside of the first leg, and an indwelling catheter disposed at least partially in and extending through the lumen of the side arm and out of the valved fenestration and along a length of the stent graft to the nose cone; and
   wherein all portions of the stent graft, with the indwelling catheter, are disposed as a single over the inner cannula and within the sheath of the single delivery device prior to delivery to the patient.

2. The stent graft delivery system of claim 1, wherein the side arm extends from the first fenestration in a distal direction and partially helically around the first leg.

3. The stent graft delivery system of claim 2, wherein the first leg is longer than the second leg.

4. The stent graft delivery system of claim 1, wherein the nose cone has a longitudinal groove and a proximal portion of the indwelling catheter resides within the groove and is held there by the retractable sheath.

5. The stent graft delivery system of claim 4, wherein the proximal portion of the indwelling catheter is pre-curved.

6. A stent graft delivery system comprising:
   a stent graft having a predeployment configuration and a deployed configuration, the stent graft having a proximal end, a distal end, wherein the stent graft is one undivided piece from the proximal end to the distal end, the stent graft comprising: ,
  a first tubular portion having a proximal end and a distal end,
  a bifurcation extending from the first tubular portion distal end,
  a first leg extending from the bifurcation and having a side wall,
  a second leg shorter than the first leg extending from the bifurcation, a fenestration in the side wall of the first leg between its proximal and distal ends,
  an aperture in the side wall of the first leg between its proximal and distal ends and disposed substantially opposite the fenestration,
  an at least partially helical side arm attached to the side wall and extending from the fenestration,
  a valve disposed over the aperture, the valve having a proximal closed portion, a distal portion, an open configuration and a closed configuration, wherein both the open and closed configuration, the proximal closed portion remains closed and substantially prevents fluid from flowing through the aperture;
  an indwelling catheter disposed at least partially within the lumen of the side arm and out of the aperture, and
  a single deployment device including a retractable sheath having an inner lumen, wherein all portions of the stent graft, along with the indwelling catheter disposed at least partially within the lumen of the side arm and out of the aperture, are disposed together within the sheath in the predeployment configuration prior to delivery of the single stent graft to the patient.

7. The stent graft delivery system of claim 6, wherein the side arm is at least partially corrugated.

8. The stent graft delivery system of claim 7, wherein the side arm extends at least partially helically about the first leg.

9. The stent graft delivery system of claim 6, wherein the valve comprises a flap of graft material.

10. The stent graft delivery system of claim 9, wherein the indwelling catheter holds the valve in the open configuration.

11. A stent graft delivery system comprising:
  a stent graft having a predeployment configuration and a deployed configuration, the stent graft having a proximal end, a distal end, wherein the stent graft is one undivided piece from the proximal end to the distal end, the stent graft comprising:
    a first tubular portion having a proximal end and a distal end,
    a bifurcation extending from the first tubular portion distal end,
    a first leg extending from the bifurcation and having a side wall,
    a second leg extending from the bifurcation, wherein the first leg is longer than the second leg,
    a fenestration in the side wall of the first leg between its proximal and distal ends,
    an aperture in the side wall of the first leg between its proximal and distal ends and disposed substantially opposite the fenestration,
    a side arm attached to the side wall and extending from the fenestration;
  an indwelling catheter disposed at least partially within the lumen of the side arm and out of the aperture and along side the stent graft toward the stent graft proximal end, and
  a single deployment device including a retractable sheath having an inner lumen, wherein all portions of the stent graft, along with the indwelling catheter, are disposed together within the sheath in the predeployment configuration prior to delivery of the stent graft to the patient.

12. The stent graft delivery system of claim 11, wherein the delivery device has a nose cone at the proximal end of the delivery device and the delivery device extends to the nose cone.

13. The stent graft delivery system of claim 12, wherein the nose cone comprises a longitudinal groove and where a portion of the indwelling catheter is disposed within the longitudinal groove and held there by the retractable sheath in the predelivery configuration.

14. The stent graft delivery system of claim 13, wherein a proximal end of the indwelling catheter is curved and held in a straightened configuration within the groove in the predelivery configuration.

15. The stent graft delivery system of claim 11, wherein the side arm is corrugated.

16. A stent graft system comprising:
  a stent graft having a predeployment configuration and a deployed configuration, the stent graft having a proximal end, a distal end, wherein the stent graft is one undivided piece from the proximal end to the distal end, the stent graft comprising, as a single piece from the proximal end to the distal end:
    a first tubular portion having a proximal end and a distal end,
    a bifurcation extending from the first tubular portion distal end,
    a first leg extending from the bifurcation and having a side wall,
    a second leg extending from the bifurcation, wherein the first leg is longer than the second leg,
    a fenestration in the side wall of the first leg between its proximal and distal ends,
    an at least partially helical side arm extending from the fenestration,
  an indwelling catheter disposed at least partially within the lumen of the at least partially helical side arm and out of the aperture and along side the stent graft toward the stent graft proximal end, and
  a single deployment device including a single sheath having an inner lumen, wherein the first tubular portion, the bifurcation, the first leg, the second leg, the fenestration, the at least partially helical side arm, and the indwelling catheter are all disposed together within the single sheath in the predeployment configuration prior to delivery of the single stent graft to the patient.

* * * * *